US008865179B2

(12) United States Patent
Chen

(10) Patent No.: US 8,865,179 B2
(45) Date of Patent: Oct. 21, 2014

(54) APTAMERIC IGE PEPTIDES IN A PROTEIN SCAFFOLD AS AN ALLERGY VACCINE

(75) Inventor: Swey-Shen Alex Chen, San Diego, CA (US)

(73) Assignee: Swey-Shen Alexchen, San Diego, CA (US)

( * ) Notice: Subject to any disclaimer, the term of this patent is extended or adjusted under 35 U.S.C. 154(b) by 487 days.

(21) Appl. No.: 12/011,303

(22) Filed: Jan. 26, 2008

(65) Prior Publication Data

US 2009/0226899 A1 Sep. 10, 2009

(51) Int. Cl.

| | |
|---|---|
| *A61K 39/00* | (2006.01) |
| *G01N 33/68* | (2006.01) |
| *C07K 16/42* | (2006.01) |
| *C07K 14/705* | (2006.01) |

(52) U.S. Cl.
CPC ........ *G01N 33/6845* (2013.01); *C07K 16/4291* (2013.01); *C07K 2318/00* (2013.01); *C07K 2317/50* (2013.01); *C07K 2316/52* (2013.01); *C07K 14/70503* (2013.01); *C07K 2319/00* (2013.01); *G01N 33/6878* (2013.01); *Y10S 424/805* (2013.01); *Y10S 424/81* (2013.01)
USPC ..................... 424/185.1; 424/192.1; 424/805; 424/810; 530/387.3; 435/7.1

(58) Field of Classification Search
None
See application file for complete search history.

(56) References Cited

U.S. PATENT DOCUMENTS

| | | | | |
|---|---|---|---|---|
| 5,583,202 | A | 12/1996 | Zanetti | |
| 6,589,741 | B2 | 7/2003 | Pluckthun et al. | |
| 6,610,297 | B1 * | 8/2003 | Kricek et al. | 424/178.1 |
| 6,620,587 | B1 | 9/2003 | Taussig | |
| 6,811,782 | B1 * | 11/2004 | Wang et al. | 424/185.1 |
| 2003/0170229 | A1 * | 9/2003 | Friede et al. | 424/130.1 |
| 2006/0052592 | A1 * | 3/2006 | Levinson et al. | 536/23.1 |

OTHER PUBLICATIONS

Chen et al., FASEB Journal, (May 14, 2004) vol. 18, No. 8, Suppl. S, pp. C173.*
Chen et al., J Immunol Methods. Apr. 20, 2008;333(1-2):10-23. Epub Nov. 20, 2007.*
Gerloni, M., W. R. Baliou, R. Billetta, and M. Zanetti. 1997. Immunity to *Plasmodium falciparum* malaria sporozoites by somatic transgene immunization. Nat.Biotechnol. 15:876-881.
Xiong, S. M. Gerloni, and M. Zanetti. 1997. Engineering vaccines with heterologous B and T cell epitopes using immunoglobulin genes. Nat.Biotechnol. 15:9:882-886.
Skerra, A. 2000. Engineered protein scaffolds for molecular recognition. J. Mol. Recog. 13:167-187.
Binz, H. K., and A. Pluckthun. 2005. Engineered proteins as specific binding reagents. Curr. Opin. Biotechnol. 16:459-469.
Parker, M. H., Y. Chen, F. Danehy, K. Dufu, J. Ekstrom, E. Getmanova, J. Gokemeijer, L. Xu, and D. Lipovsek. 2005. Antibody mimics based on human fibronectin type three domain engineered for thermostability and high-affinity binding to vascular endothelial growth factor receptor two. Prot. Eng. Des. Sel. 18:435-444.
Tsien, R. Y. 1998. The green fluorescent protein. Ann. Rev. Biochem. 67:509-544.
Yang, F., L. G. Moss, and G. N. Phillips. 1996. The molecular structure of green fluorescent protein. Nat. Biotech. 14:1246-1251.
Ormo, M., A. B. Cubitt, K. Kallio, L. A. Gross, R. Y. Tsien, and S. J. Remington. 1996. Crystal structure of the Aequorea victoria green fluorescent protein. Science 273:1392-1395.
Waldo, G. S., B. M. Standish, J. Berendzen, and T. C. Terwilliger. 1999. Rapid protein-folding assay using green fluorescent protein. Nat. Biotech. 17:691-695.
Pedelacq, J. D., E. Piltch, E. C. Liong, J. Berendzen, C. Y. Kim, B. S. Rho, M. S. Park, T. C. Terwilliger, and G. S. Waldo. 2002. Engineering soluble proteins for structural genomics. Nat. Biotech. 20:927-932.
Mattheakis, L. C., R. R. Bhatt, and W. J. Dower. 1994. An in vitro polysome display system for identifying ligands from very large peptide libraries. Proc. Natl. Acad. Sci. USA 91:9022-9026.
Hanes, J., and A. Pluckthun. 1997. In vitro selection and evolution of functional proteins by using ribosome display. Proc. Natl. Acad. Sci. USA 94:4937-4942.
He, M. and M. J. Taussig. 1997. Antibody-ribosome-mRNA (ARM) complexes as efficient selection particles for in vitro display and evolution of antibody combining sites. Nucl. Acids Res. 25:5132-5134.
Hanes, J., C. Schaffitzel, A. Knappik, and A. Pluckthun. 2000. Picomolar affinity antibodies from a fully synthetic naive library selected and evolved by ribosome display. Nat. Biotech. 18:1287-1292.

(Continued)

*Primary Examiner* — Michael Szperka

(57) ABSTRACT

A method is disclosed wherein an antigenic B-cell epitope is discovered by in vitro transcription and translation of pre-determined sequence on thermostable protein scaffolds detected by antibodies to a native protein. Immune reactivities of IgE B-cell epitopes from pre-determined IgE sequences from the constant region, engaged in binding to high affinity IgE Fc receptors, placed in a loop of green fluorescent protein (GFP) were shown immuno-reactive with anti-IgE. Moreover, the antigenic B-cell epitope can be further optimized by molecular evolution, selected by conformer antibody and receptor on solid phase via ribosome display. Alternatively, a random aptameric antigenic sequence inserted into a loop of the protein scaffold, mimicking a pre-determined sequence of a native protein, can be selected by solid phase conformer antibody and receptor via ribosome display. High affinity binding of B-cell epitopes selected from the random aptameric library with antibodies to native pre-determined B-cell epitope of a native protein can be optimized by molecular evolution with error-prone RT-PCR by ribosome display.

14 Claims, 8 Drawing Sheets

(56) References Cited

OTHER PUBLICATIONS

Yang, Y.-M., Barankiewicz, T.J., He, M., Taussig, M., and Chen, S.-S. 2007. Selection of antigenic markers on a GFP-Ck fusion scaffold with high sensitivity by eukaryotic ribosome display. B.B.R.C. 359: 251-257.

Garman, S. C., B. A. Wurzburg, S. S. Tarchevskaya, J. P. Kinet, and T. S. Jardetzky. 2000. Structure of the Fc fragment of human IgE bound to its high-affinity receptor Fc epsilonRI alpha. Nature 406:259-266.

Robertson, M. W. 1993. Phage and *Escherichia coli* expression of the human high affinity immunoglobulin E receptor alpha-subunit ectodomain. Domain localization of the IgE-binding site. J. Biol. Chem. 268:12736-12743.

Vangelista, L., S. Laffer, R. Turek, H. Grönlund, W. R. Sperr, P. Valent, A. Pastore, and R. Valenta. 1999. The immunoglobulin-like modules Cepsilon3 and alpha2 are the minimal units necessary for human IgE-FcepsilonRI interaction. J. Clin. Invest. 103:1571-1578.

Keown, M. B., R. Ghirlando, G. A. Mackay, B. J. Sutton, and H. J. Gould. 1997. Basis of the 1:1 stoichiometry of the high affinity receptor Fc epsilon RI-IgE complex. Eur. Biophy. J. 25:471-476.

Mahler, V., S. Vrtala, O. Kuss, T. Diepgen, R. Suck, O. Cromwell, H. Fiebig, A. Hartl, J. Thalhamer, G. Schuler, D. Kraft, and R. Valenta. 2004. Vaccines for birch pollen allergy based on genetically engineered hypoallergenic derivatives of the major birch pollen allergen, Bet v 1. Clin. Exp. Allergy 34:115-122.

Garman, S. C., J. P. Kinet, and T. S. Jardetzky. 1998. Crystal structure of the human high-affinity IgE receptor. Cell 95:951-961.

Christmann, A., K. Walter, A. Wentzel, R. Kratzner, and H. Kolmar. 1999. The cystine knot of a squash-type protease inhibitor as a structural scaffold for *Escherichia coli* cell surface display of conformationally constrained peptides. Protein Eng. 12:797-806.

Haack, T., J. A. Camarero, X. Roig, M. G. Mateu, E. Domingo, D. Andreu, and E. Giralt. 1997. A cyclic disulfide peptide reproduces in solution the main structural features of a native antigenic site of foot-and-mouth disease virus. Intern. J. Biol. Macromol. 20:209-219.

Zaccolo, M., and E. Gherardi. 1999. The effect of high-frequency random mutagenesis on in vitro protein evolution: a study on TEM-1 beta-lactamase. J. Mol. Biol. 285:775-783.

Boder, E. T., K. S. Midelfort, and K. D. Wittrup. 2000. Directed evolution of antibody fragments with monovalent femtomolar antigen-binding affinity. Proc. Natl. Acad. Sci. USA 97:10701-10705.

Kozak, M. 1999. Initiation of translation in prokaryotes and eukaryotes. Gene 234:187-208.

Worn, A., and A. Pluckthun. 2001. Stability engineering of antibody single-chain Fv fragments. J. Mol. Biol. 305:989-1010.

Nieba, L., A. Honegger, C. Krebber, and A. Pluckthun. 1997. Disrupting the hydrophobic patches at the antibody variable/constant domain interface: improved in vivo folding and physical characterization of an engineered scFv fragment. Prot. Eng. 10:435-444.

Jung, S., A. Honegger, and A. Pluckthun. 1999. Selection for improved protein stability by phage display. J. Mol. Biol. 294:163-180.

Worn, A., and A. Pluckthun. 1998. Mutual stabilization of VL and VH in single-chain antibody fragments, investigated with mutants engineered for stability. Biochemistry 37:13120-13127.

Proba, K., A. Worn, A. Honegger, and A. Pluckthun. 1998. Antibody scFv fragments without disulfide bonds made by molecular evolution. J. Mol. Biol. 275:245-253.

Troth, R. L., K. Harper, M. A. Mayo, and L. Torrance. 1999. Fusion proteins of single chain variable fragments derived from phage display libraries are effective reagents for routine diagnosis of potato leafroll virus infection in potato. Phytopathol. 89:1015-1021.

He, M., and M. Taussig. 2005. Ribosome display of antibodies: expression, specificity and recovery in a eukaryotic system. J Immunol Meth. 297:73-82.

* cited by examiner

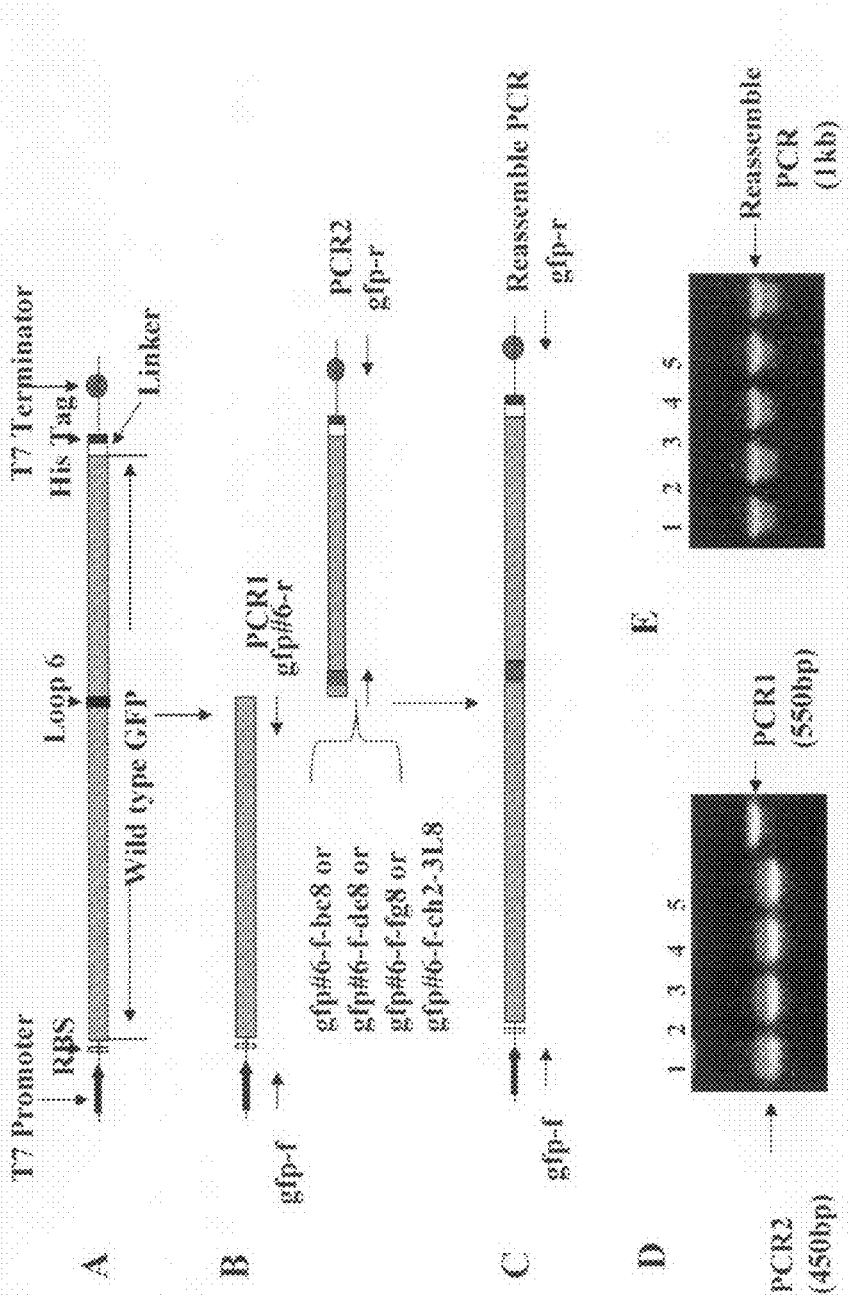

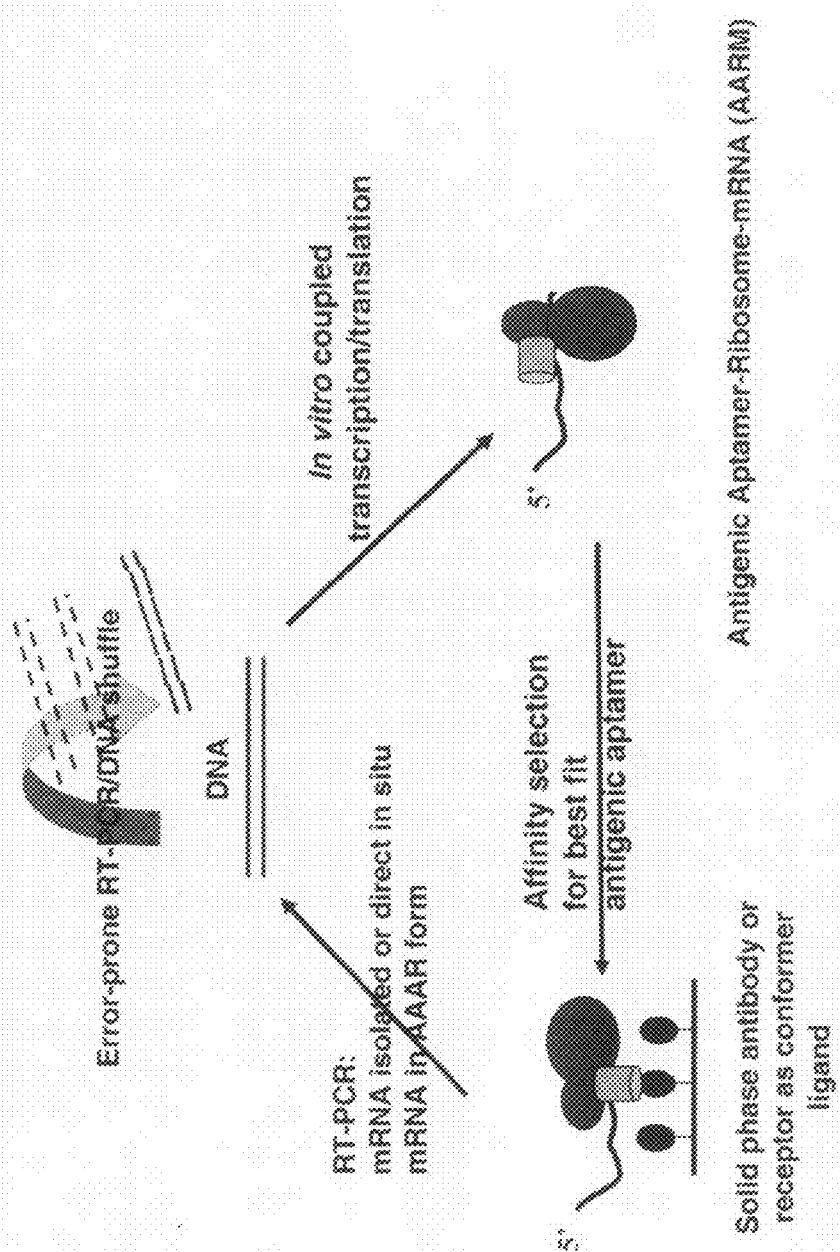

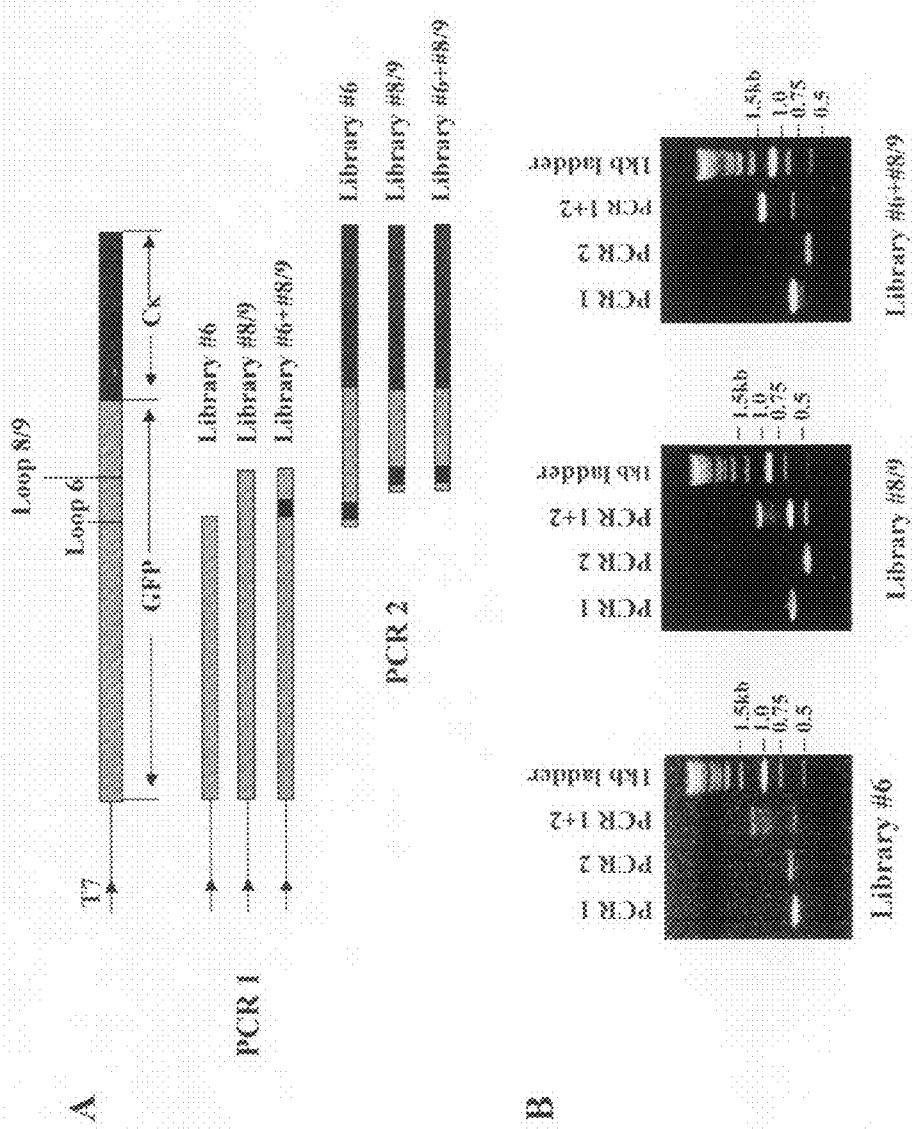

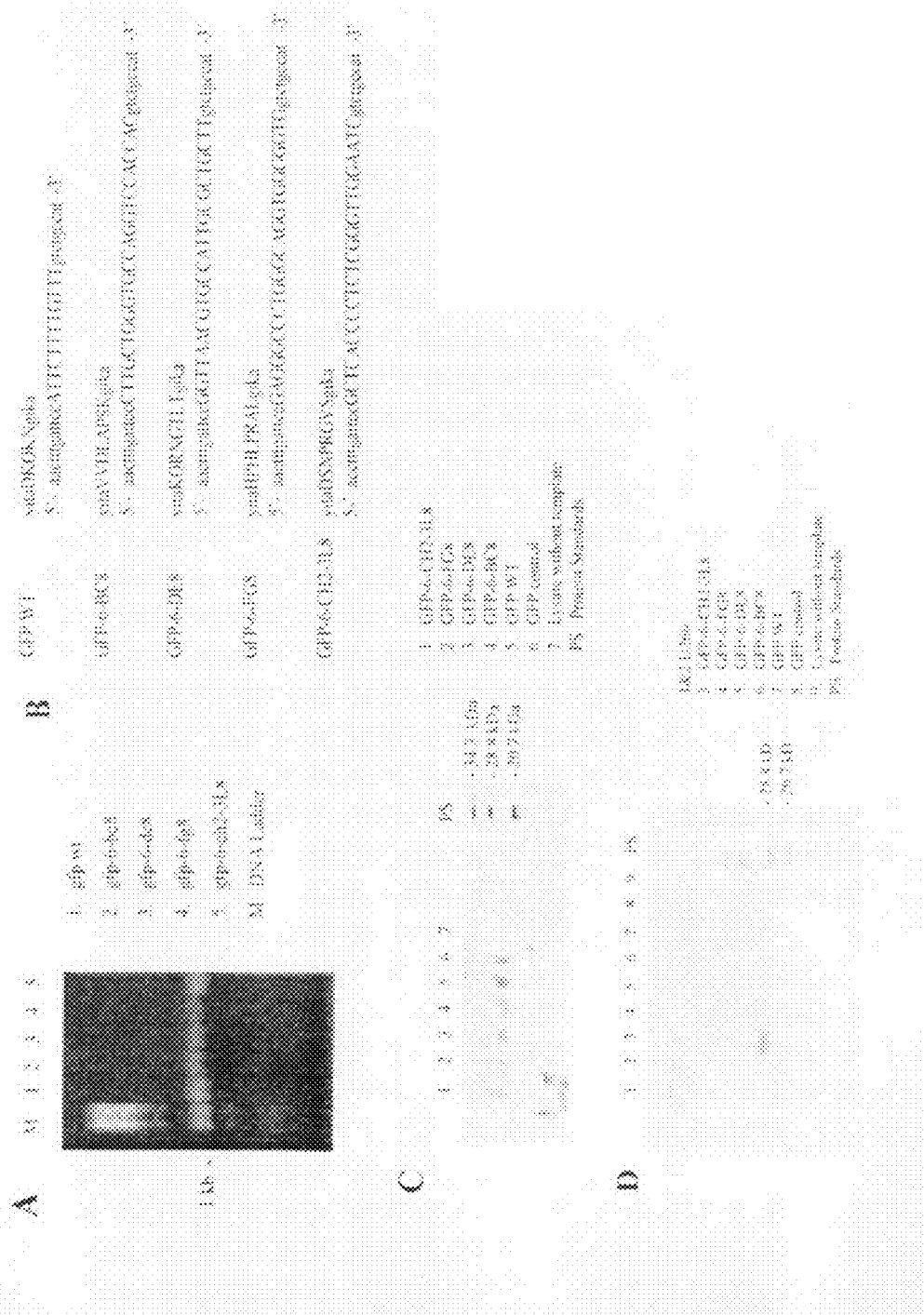

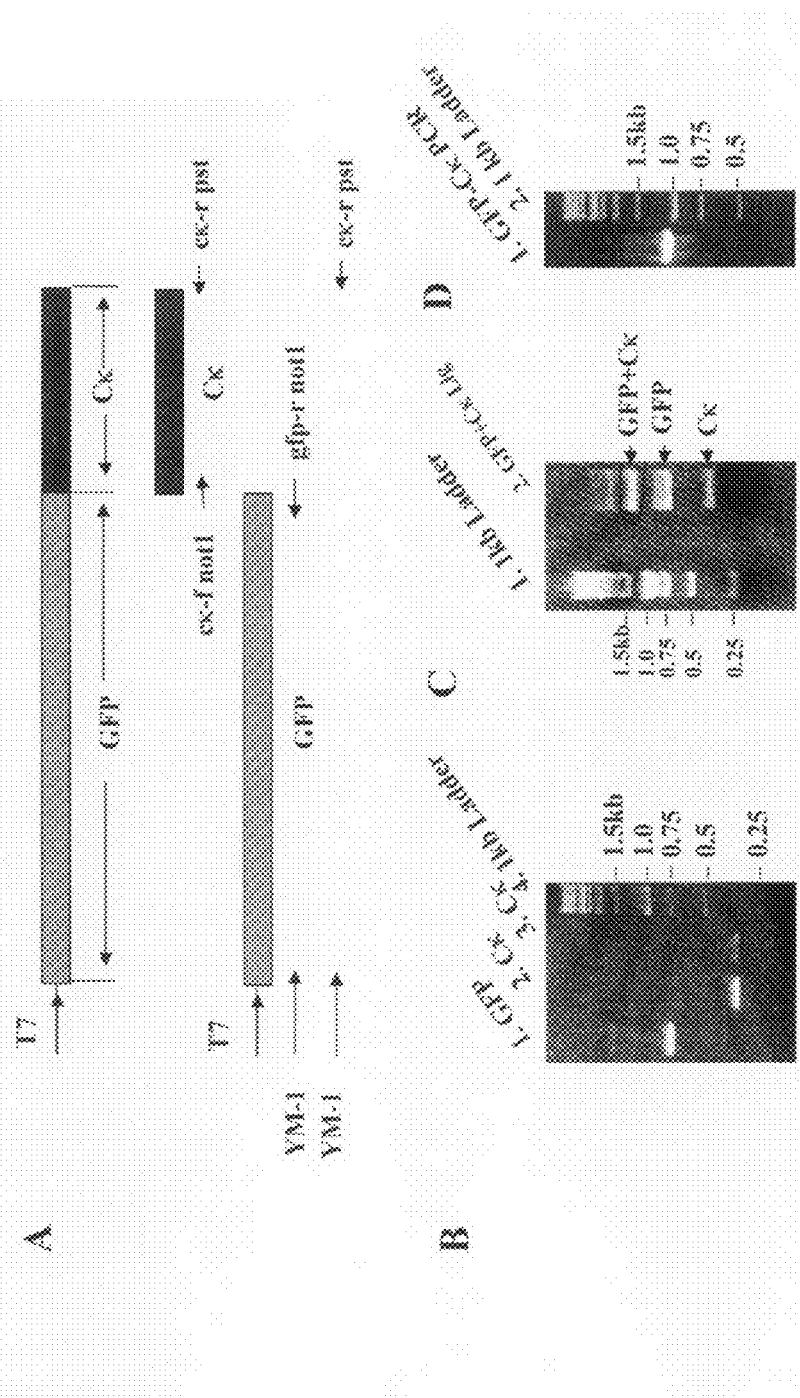

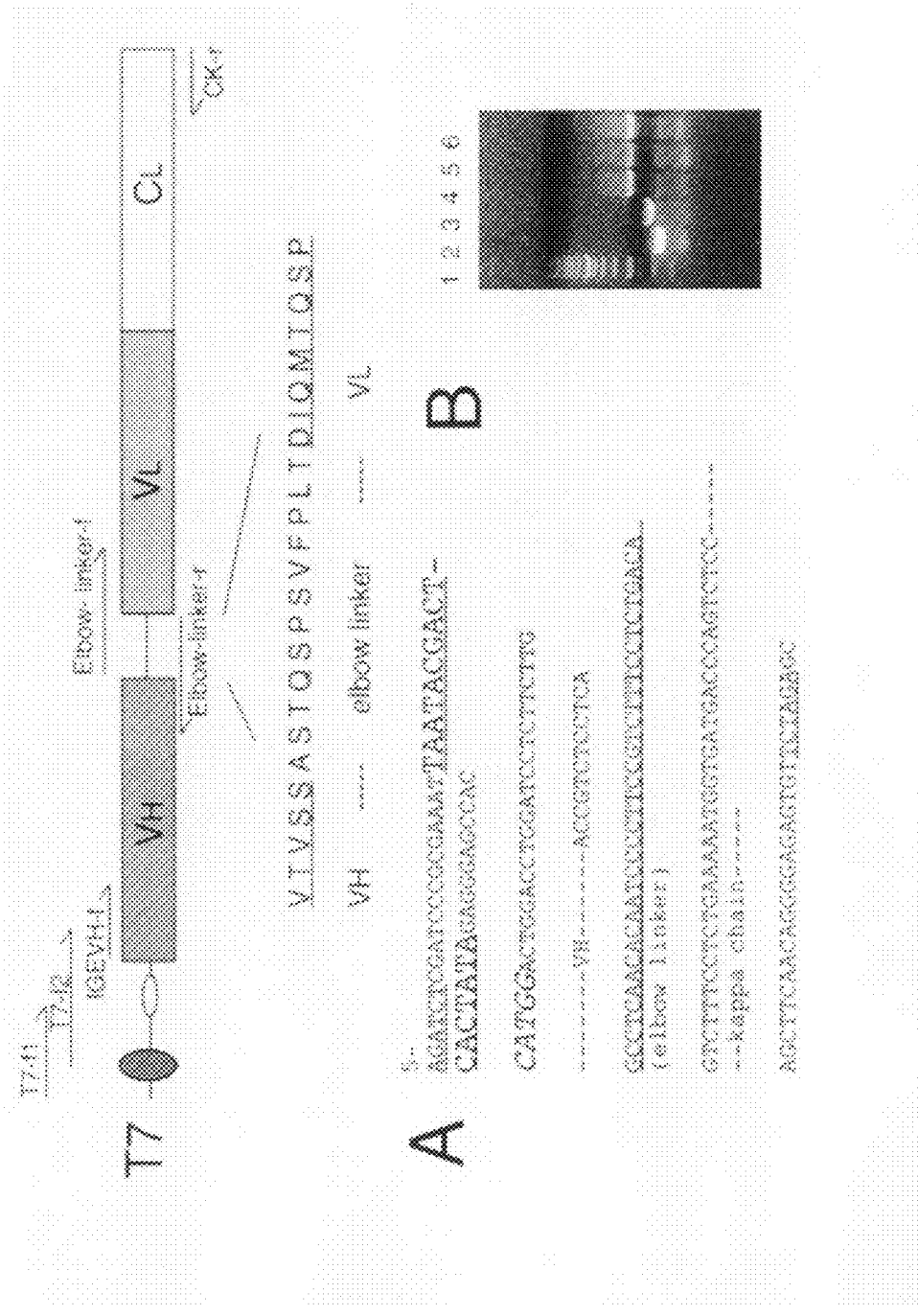
Fig. 6 Assembly of ScFv DNA template

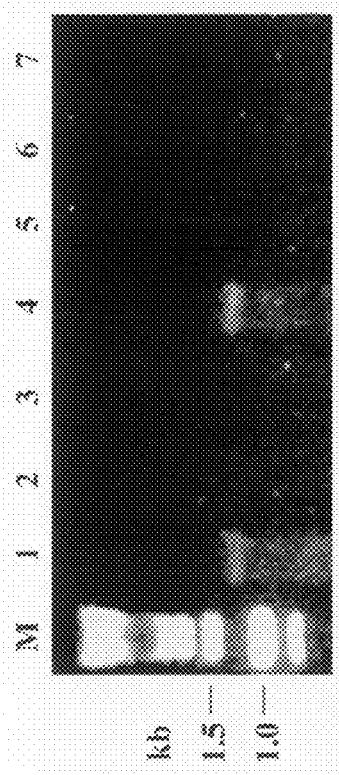
Fig. 7 Selection of GFP and Cκ antigenic epitopes by ribosome display

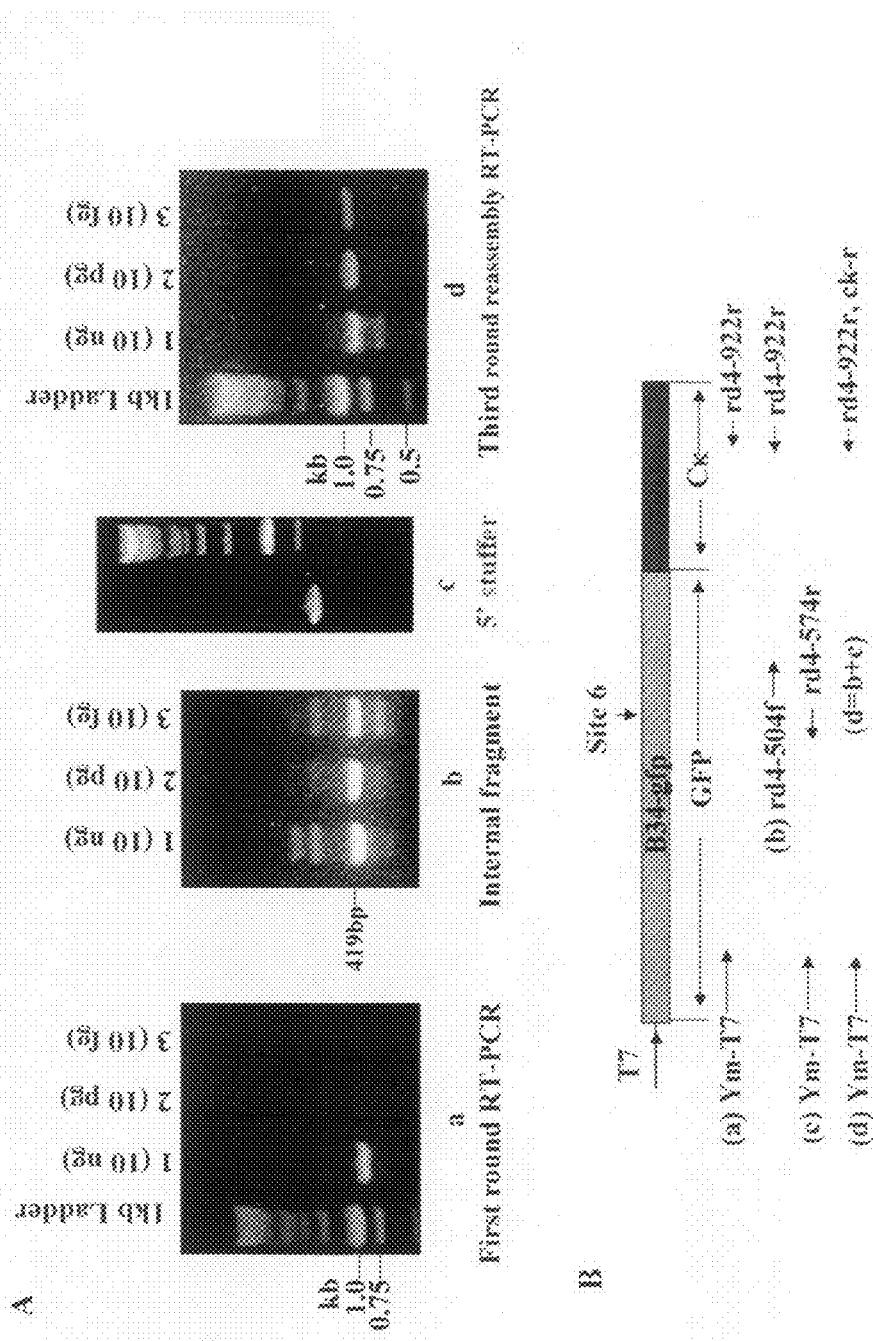
Fig. 8 Reiterative rounds of selection of monospecific B34 epitope on solid phase MAb anti-GFP by ribosome display

US 8,865,179 B2

APTAMERIC IGE PEPTIDES IN A PROTEIN SCAFFOLD AS AN ALLERGY VACCINE

BACKGROUND OF INVENTION

1. Field of Invention

A systematic method is presented for discovering and determining the suitable conformation of a mono-specific B-cell epitope appropriate for eliciting a protective antibody response.

2. Description of the Related Arts

Lack of definition of a mono-specific B-cell epitope The heterogenic antibody responses to complex protein antigens frequently lead to futile protective immune response. There is an urgent need for understanding the entity of protective antigen, and even the fine specificity, i.e., the mono-specific B-cell epitope of the protective antigen. To identify the mono-specific B-cell epitope as therapeutic target is important due to the plethora and complexity of B-cell epitopes in a complex biological macromolecule from pathogenic microbes, toxins, and cancer cells. In particular, suboptimal antibody responses to a protective B-cell epitope may ensue as a result of antigen competition and downregulation of response to this particular protective B-cell epitope due to presence of a myriad of other multiple B-cell epitopes.

Thus far, there does not exist a systemic method to first delineate such mono-specific B-cell epitopes, and second to conform and improve these B-cell epitopes for a high affinity interaction with antibodies. Most studies employ the overlapped synthetic peptide sequences, and couple each respective peptide to the carrier protein for raising mono-specific antibody. For decades, B-cell epitopes can not be simply synthesized and coupled onto carrier protein for studying their native antigenicity. Antibodies raised by this method while adequate for reactive with denatured proteins according to western blot analysis, are generally incapable of reacting with native proteins, and therefore are useless for potential higher impact for neutralizing toxins, microbes or cancerous cells.

Understanding and subsequently utilizing B-cell epitopes as well-defined vaccine can improve vaccine efficacies. Linear peptides synthesized from regions of protein, including solvent exposed loop region according to the X-ray structure of a protein, and coupled to immunogenic carrier protein for immunization, were known to induce antibodies that react with linear peptide or denatured protein but are not cross-reactive with the native protein.

Protein Scaffold and stability The desirable loop sequences spanning part of the scaffold protein are characterized by hydrophilicity in nature, surface-exposed, and mobile. It is known that foreign B-cell antigenic loops grafted in complementarity-determining regions (CDR) of the immunoglobulin scaffold, exhibit constrained antigenic conformations similar to those expressed as the native loop of parent molecules. This process of "antigenization of antibody" utilizes the immunoglobulin fold as a scaffold to constrain a grafted oligopeptide (Zanetti, Antigenized antibodies and genes, U.S. Pat. No. 5,583,202; Gerloni et al., 1997 Nat. Biotech. 15: 876; Xiong et al., 1997. Nature Biotech. 15:882). CDR regions of immunoglobulin are thermodynamically less resilient to inserted foreign determinants into the existing loop sequence with solubility affected. Although in most case immunoglobulin scaffold is successful for presenting the linear sequence-dependent epitope for inducing cytotoxic T-lymphocytes. The issue remains open as to the appropriate scaffolding protein for constraining conformation-dependent B-cell epitopes.

In addition to CDR3 of immunoglobulin scaffold, proteins of super-immunoglobulin gene family, i.e., CTLA4, fibronection domain have also been tested as protein scaffold (Skerra, 2000. Mol. Reg. 13:167; Binz and Pluckthun, 2005 Curr. Opin. Biotech. 16:459). These proteins exhibiting β-pleated sheet immunoglobulin fold, also display similar range of melting temperatures to that of immunoglobulin as a heat labile protein. Although CTL-A4 and fibronectin were employed for inserting an aptameric peptide library of random specificities in the loop region since only the conformationally viable species will participate in the selection process at the expense of pre-selection of library repertoire.

However for inserting a peptide of pre-determined sequence such as the loop sequences from the X-ray structure of a protein, each relevant sequence in each protein is unique and non-replaceable, and there is stringent demand for successfully constraining such unique pre-determined sequences. Therefore, a reliable thermostable protein scaffold that provides high probability of constraining capacity for pre-determined amino acid sequence becomes a necessity for antigenic systems-discovery platform.

SUMMARY OF THE INVENTION

The antigenic systems-discovery requires determination of a thermostable protein scaffold that harnesses a mono-specific B-cell epitope that also permits its molecular evolution for a best fit B-cell epitope. The four cardinal embodiments of the present invention are:

1. Choice of a Highly Thermostable Protein Scaffold to Confine the Inserted Aptamer Protein scaffold for GFP is a stable proteolysis-resistant single chain of 238 amino acids exhibiting an 11-stranded β-barrel wrapped around a single central helix (Tsien, 1998. Ann. Rev. Biochem. 67:509; Yang et al., 1996. Nat. Biotech. 14: 1246; Ormo et al., 1996. Science. 273: 1392; Waldo et al. Nature Biotech. 17: 691), and the fluorescence property is dependent on the thermostability of folding of aptameric GFP. According to both renaturation kinetics and fluorescence emission, GFP is highly stable and resists protein denaturation even at 70° C. heating over 30 min (Tsien, 1998. Ann. Rev. Biochem. 67:509; Waldo et al. Nature Biotech. 17: 691; Pedelacq et al., 2002. Nat. Biotech. 20: 927). Therefore, we make a decision to choose the highly stable backbone of GFP as the scaffold for inserting aptameric peptides. Given the capacity of GFP to constrain its own native thermostable B-cell epitopes, the thermostability of GFP can be fully extended and utilized in an antigenic B-cell epitope systems-discovery.

The establishment of an epitope in GFP scaffold approximates that of native protein is initially determined by its ability to be recognized by antibodies. The validation is then completed in a reciprocal manner when the antigenized GFP is tested to raise antibodies that react with the native protein. This will critically establish the 'near identity' of the pre-determined sequences scaffold by GFP to be relevant to the moiety present on the native protein. Yet this leaves open the issue whether the antigenized GFP elicit an antibody response better than the native antigenic ligand; moreover one may not anticipate that every antigenized aptamer should yield a recognizable antigenic determinants by monoclonal or polyclonal antibodies despite the thermostability of the scaffold. The thermodynamic property of folding exceeds rational anticipation.

2. Choice/Replication of the Best Fit Conformed Antigen in the Pre-Determined Aptameric Protein Fusion Scaffold Adapted on Ribosome Display.

In order to have the antigenized GFP reliably matches or exceeds the performance of native antigenic ligand, and more importantly ensures that aptameric GFP with pre-determined sequences remains recognizable by antibodies, a step of molecular selection coupled to molecular evolution is embodied in this invention. This takes into consideration of adapting aptameric GFP on a special format of ribosome display, permitting selectable fitness via molecular evolution.

In principle, The design of a B-cell antigenic epitope systems-discovery platform herein embodies two essential and necessary attributes in that first, there must exist a best choice of this protein scaffold based on its thermostability so that it constrains and presents the inserted peptide onto the molecular graft close to native conformation similar to that inherent in the parental protein. Second, the sequence inserted must in turn be mutatable and therefore yields a best fit aptameric sequence (apt-, fit) to mimic the antigenic structure preserved on the native protein in its original configuration.

Henceforth the embodied invention herein constrains the conformation of the inserted antigenic epitope within the loop of a protein scaffold. The constrained conformation is such as to be capable of a high affinity interaction with antibodies to the native protein, or with a cognate receptor prepared on the solid phase platform. Thus the embodiment of the invention is to provide a pre-determined amino acid sequences within a thermostable protein scaffold with a high melting temperature.

Furthermore, the selective platform is designed as such to enable the transcription and translation of the protein scaffold with the pre-determined sequence such that the translated protein retaining the mRNA can be selected on solid phase antibody or receptor. Thus, the embodiment of this invention with the retention of mRNA along with protein can ensure that a best-fit antigen be initially determined or later also molecularly evolved by altering the sequences of mRNA due to the phenotype/genotype-linked solid phase platform technology.

Ribosome display adapted into the present systems-discovery platform, is a validated, cell-free system based on genotype/phenotype-linked selection of proteins and their encoding mRNA, following binding to ligands immobilized on solid surfaces (Taussig and He, 2003. Ribosome complexes as selection particles for in vitro display and evolution of proteins. U.S. Pat. No. 6,620,587; Mattheakis et al., 1994. PNAS. 91: 9022; Hanes and Pluckthun. 1997. PNAS. 94:4937; He and Taussig, 1997. N.A.R. 25: 5132). In general, this platform addresses protein-protein interactions of all categories.

In the specific embodied application, this format will be adapted to improve interactions of the pre-determined aptameric B-cell epitopes with antibody or receptor molecules. The improvement is based on enabling mutation into the pre-determined aptameric sequence via error-prone PCR of the ribosome-bound mRNA. Residue changes in the pre-determined aptameric region can be accomplished via RT-PCR reactions. The higher affinity interaction due to the substitutions of aptameric residues can be selected in turn by binding to the antibody or receptor in the presence of competing native ligand that accommodates this natural sequence in the parent native ligand.

The thermostability of the constraining GFP protein scaffold should conform a majority of pre-determined amino acid sequences. Thus even in case of very low affinity of pre-determined sequence beyond the detection limit of antibodies/receptors, modification of existing pre-determined core sequence by error-prone PCR can result in critical substitutions of key residues to overcome the threshold of detectable interactions. This critical improvement will set the stage of further high affinity evolution by successive rounds of RT-PCR reactions according to ribosome display format.

3. Choice/Replication of the Best Fit Conformed Antigen in the Random Aptameric Protein Fusion Scaffold Adapted on Ribosome Display.

In case of the strict non-conformability of a given pre-determined aptameric peptide, which is not even rescuable by error-prone PCR, conducted on ribosome display above the threshold of interactions with antibodies or receptors, a library of random aptameric peptidic sequences in its stead can be inserted into the scaffold fusion protein in the selectable ribosome display platform. This library with random oligonucleotides with appropriate length will accommodate a diverse library of $10^{12-14}$ in sizable geometric three-dimensional shapes.

In this embodiment, the appropriately selected, transcribed and translated subgroups of random amino acid sequences that interact with the antibodies/receptors may entail the conformable geometric shape for the antibodies/receptors. Henceforth this selective platform will be suitable for selecting a conformable B-cell epitopes above the threshold of detection for interacting with solid phase antibodies/receptor from the sizable library.

Thus embodiment of the random aptameric library of random amino acid sequences overcomes the restriction imposed on pre-determined core amino acid sequences described above. Likewise, the ribosome display format permits further the enablement that mutation (s) be introduced into the randomly selected aptameric sequence via error-prone PCR of the ribosome-bound mRNA. The higher affinity interaction due to the substitutions of aptameric residues can be selected in turn by binding to the antibody in the presence of competing native antigen.

4. Improvement on Antigen Systems-Discovery on CDR-Based Fusion Scaffold on Ribosome Display Platform Complementarity-determining region (CDR) of immunoglobulin can also serve as the site for accommodating the foreign pre-determined amino acid sequences (Zanetti, Antigenized antibodies and genes, U.S. Pat. No. 5,583,20), this embodiment of invention herein makes improvement on employing CDR region for placing aptameric pre-determined amino acid sequences. First, the embodiment of the invention is to substituting the aptameric peptide sequence in the CDR region, while displacing the native CDR sequence, instead of insertion of a foreign sequence further on top of the native CDR sequence, since CDR region has a limited capacity for accommodating certain length of peptide sequences.

Second, the invention embodies the pre-determined peptide B-cell epitope in the CDR region of the single chain Fv antibody, VHк (scFv: VHк) on the ribosome display format. This platform enables antigenic epitope improvement of the existing pre-determined sequence via introduced change of the amino acid with the error-prone PCR via a high affinity interaction with solid phase antibodies/receptor according to the ribosome display format.

Third, the embodiment of the sizable random library will compensate for the failure of exhibition of pre-determined peptide antigenic B-cell epitopes. CDR regions with incompatible sequences will affect immunoglobulin folding and denaturation due to thermolabile nature of immunoglobulin as the protein scaffold; henceforth, a significant pre-determined sequence is thus precluded from entering the effective selectable pool. This lack of presentation of the incompatible group of pre-determined sequences can be compensated by sizable library consisting of random amino acid sequences, even though the de facto CDR library is smaller than that of aptameric antigenic library accommodated by GFP due to inherent difference of thermostability of protein scaffold.

Fourth, the embodiment of mutatable CDR selectable library in the special single chain Fv antibody (VHκ) on the ribosome display format offers further advantage of improvement of the selected random aptamer by molecular evolution.

DETAILED DESCRIPTION OF THE INVENTION

1. Specification of Antigenized Pre-Determined IgE B-Cell Epitopes in GFP Scaffold in an In Vitro High-Throughput Protein Platform Via B-Cell Epitope Immunization Test (BEIT)

Conventional cloning and expression in the prokaryotic and eukaryotic vectors are labor-intensive and time-consuming for completing the assessment of the immunogenicity. We devise a strategy to bypass the requirement of these two steps. The immunogenicity of the replaced, inserted or substituted B-cell epitopes of in the protein scaffold can be expediently tested as in vitro transcribed and translated product.

In this embodiment, the stretches of amino acid sequences of peptides of potential antigenicity inserted into a scaffold protein or scaffold fusion protein are called aptamers ("apt"—adapt from Latin) as an inserted candidate sequence obtained from any given protein. The first stage of the embodiment resides in constructing a series of aptameric antigenic peptidic sequences in the number of five to twenty residues in length either by direct insertion or via replacement of the native loop, into a replicable, transcribing protein scaffold. The high throughput platform of protein scaffold is constructed by installing transcription-enabled sequence and translation-enabled sequence onto it. The dual enablement permits the scaffold protein with aptameric peptide sequence, readily transcribed and translated in vitro in a test tube or a 96-well bypassing molecular cloning and expression, in the bacteria or yeast biologic organism.

In this embodiment, a highly thermostable protein scaffold, the green fluorescent protein (GFP) accommodates the inserted antigenic aptamers in the scaffold. GFP is a stable proteolysis-resistant single chain of 238 amino acids exhibiting an 11-stranded β-barrel wrapped around a single central helix (Tsien, 1998. Ann. Rev. Biochem. 67:509; Yang et al., 1996. Nat. Biotech. 14: 1246; Ormo et al., 1996. Science. 273: 1392; Waldo et al. Nature Biotech. 17: 691), and the fluorescence property is dependent on the thermostability of folding of aptameric GFP. According to both renaturation kinetics and fluorescence emission, GFP is highly stable and resists protein denaturation even at 70° C. heating over 30 min (Tsien, 1998. Ann. Rev. Biochem. 67:509; Waldo et al. Nature Biotech. 17: 691; Pedelacq et al. 2002. Nature Biotech). Therefore we make a decision to choose the highly stable backbone of GFP as the scaffold for inserting aptameric peptides.

The second stage of embodiment permits ascertainment of immune specificity of an antigenic aptameric peptide in the GFP scaffold in a transcription/translation-enabled format such that retention/preservation of antigenicity of the pre-determined amino acid sequence to that of the natural antigenic B-cell epitope in the native parental protein. In this convenient enabling format, transcribed and translated aptameric antigenic protein can be assessed by polyclonal antibodies raised against the native protein. The reactivities of in vitro transcribed and translated aptameric GFP product with polyclonal antibodies depend on the constrainability of the pre-determined peptide of the given amino acid sequence.

The positive validation of the immune reactivities affirms the pre-determined peptide is thermodynamically conformable and thus can be conformed or constrained by the protein scaffold; furthermore, this affirmation indicates the aptameric protein can now be tested in vivo for eliciting antibodies that react with the pre-determined peptide sequence in the parent molecules.

Thus the correspondence of antigenicity with regards to its capacity to react with relevant antibodies as well as its capacity in eliciting antibodies to react with native antigens will ascertain the usefulness of this aptameric protein as a biologically useful vaccine in an immunization test. The biologic useful vaccines will include proteins from infectious disease microbes, biologically functional protein macromolecules, enzymes, transcription factors, and cancer cell antigens. The schematic process of inserting and evaluating aptameric peptide sequences as B-cell epitope with known pre-determined amino acid sequence in a protein scaffold for the immunization test for its potential as a useful vaccine is christened BEIT (B-cell Epitope Immunization Test).

Different regions of a protein can be selected from any given region such as the loop region, or α-helix or β-pleated sheet or the β-turn region, or a combination of the above thereof, in particular, sequences representing the regions that approximate, or overlap, or correspond exactly to binding sites of a pathogenic protein required for initiating an infection by a microbe, the binding of antibodies elicited by the aptameric protein vaccine inhibit the microbial infections, neutralizing toxins, blocking enzyme-mediated signal transduction.

Moreover, the sites of B-cell epitopes of pre-determined sequences on these proteins can be either receptors for initiating signal transduction or acceptor/biologic ligand that can bind to receptors, or enzymes involved in signal transduction. It is anticipated that in vivo antibodies raised to designed aptameric peptide antigens via the BEIT system can modulate, modify, reduce, amplify, block or inhibit biologic signal transduction of the receptor, or via blocking the acceptors/ligands in the system to achieve the modulation of the biologic system, and protect against microbial infections or cancers.

One preferred embodiment of this enabling system is by replacing pre-determined sequence into the loop of the scaffold protein by virtue of the one-tube reaction of coupling the in vitro transcription/translation procedure via a commercial kit. This strategy of replacement, i.e., replacing the original loop sequence with the pre-determined aptameric antigenic sequences in enabling the BEIT (or inserting the pre-determined sequences in the native loop) will be to insert the aptameric scaffold protein in two sequential combinatory steps: the first is to prepare a half molecule of the scaffold with the 5' end equipped with the transcription and translational enabling sequences, and this half may also consist of the 3' end of primer sequence either as the linker sequence to the next half molecule to be assembled, or may in a different embodiment contain only the anchor, complementary sequences to the next half molecule to be assembled.

The second half molecules in the 3' end preferably contain the aptameric peptide sequence(s) as bait with a few complementary sequences at the 5' proximal sequences such that these sequences are complementary and can anneal with the sequence of the first 5' half molecules. These two preferred embodiments will then be combined in a reaction involved the annealing of the two half molecules via the complementary sequences built in the 3' reverse primer of the first half molecules and the 5' forward primer of the second half molecules. A simple annealing reaction will cement these two half molecules, and the BEIT sequences contained either within the 3' reverse sequences or the 5' forward sequence To facilitate this assembly, it consists of the following three steps as shown in FIG. 1: (i) PCR1 fragment utilizing a pair of primers that amplify the half molecules spanning the T7 transcription start site or known transcription start sites known in the art documented in current protocols and molecular cloning handbook, Kozak or Shine-Dalgarno sequence and the beginning of the GFP (delineated by the 5' primer) up to the upstream GFP sequence to loop 6 (delineated by the 3' primer); (ii) PCR2 fragment utilizing 5' primer consisting of GFP sequences (that pair with the 3' primer of the first PCR fragment) that correspond to the loop regions, or the neighboring sequence of the loops or the α-helix and β-sheet or β-turn or hairpins that are involved in the conformation of the proteins; accordingly the design includes an oligonucleotide stretch from 12-30 bridging residues that are involved in the complementarity-pairing of the half molecule.

The bridging sequences are structural sequences that omit the intervening native loop sequence. Thereby via the assembly process of two fragments, the native loop sequence of the scaffold is deleted. The original loop sequence in the scaffold can be bypassed or deleted. To facilitate protein purification, either 5' or 3' peptide tag known in the art can be inserted (current protocols and molecular cloning). T7 terminator or other terminator sequence can be added at the end of the 3' primer; (iii) assembly of the two half molecules of GFP, the stuffer PCR1 fragment and PCR2, containing BEIT of choice with the aided-in tags for purification.

Thus, given the capacity of GFP to constrain conformation-dependent B-cell epitopes, the thermostability of GFP can be fully utilized in an antigenic systems-discovery. The establishment of an epitope in the GFP scaffold being approximate to that of a native protein, is initially determined by its ability to be recognized by antibodies raised to the native protein. And the transcription and translation enabled sequence permits an expedient evaluation via BEIT. Next, in a reciprocal manner, the validation of antigenicity is further extended to analysis of antigenicity in vivo in experimental animals in that antibodies raised to the antigenized GFP can also react with the native protein. This will critically establish the 'near identity' of the pre-determined amino acid sequence, B-cell epitope, scaffolded by GFP to be relevant to the moiety present on the native protein.

Moreover, it will be tested whether the antigenized GFP elicits an antibody response comparable to or better than the native antigenic ligand; moreover one may not anticipate that every antigenized aptameric peptide should yield an antigenic determinant recognizable by monoclonal or polyclonal antibodies despite the thermostability of the scaffold. The constraining property of folding may yield a conformed B-cell epitope suboptimal, or comparable, or under molecular evolution in the next generation may even exceed the native conformation present in native protein. In conclusion, the first generation of BEIT will determine a qualitative assessment of whether or not the peptide aptamer in the BEIT prepared in the conformation above will work.

2. Optimization of Aptameric Peptide Antigenic Epitope of BEIT

Next, the invention embodies the molecular platform of ribosome display integrated with BEIT in improving B-cell epitopes as the integral antigenic epitope discovery system. As shown in FIG. 2, the advantage of integrating BEIT into the ribosome display platform resides in selection and further re-engineering the aptameric antigen ribosome message (AARM) complex for a better fit to the solid phase conformer antibodies/receptors via error-prone RT-PCR. RT-PCR employed in recovering the mRNA associated with aptameric antigenic protein scaffold, renders a change or cumulative changes of the aptameric peptide sequences under selection so that the second generation of antigenic aptameric peptides is conformed, in a snug fit, to the binding sites of solid phase conformer as a result of mutations introduced into the aptameric region via the ribosome display.

This preferred embodiment further improves the precision of BEIT via a process of in vitro selection shaped by antibodies or receptors coated on solid phase as conformers. The embodiment of molecular evolution will yield preferentially the molecularly evolved AARM, whose phenotype and genotype are physically coupled for antibodies/receptors selection on the solid phase. As shown in FIG. 2, the change of genotype is implemented by designed mutagenesis, or errors introduced by RT-PCR of mRNA attached to the aptameric protein antigens of the AARM complexes. And by virtue of this genotype/phenotype-associated affinity selection of antigen-antibody reactions, the fittest aptameric antigenic epitope selected by solid phase conformers will eventually be chosen as vaccines, with the knowledge of its molecularly altered genetic codes acquired during molecular evolution that contributes to reshaping a high affinity of aptameric antigen to the solid phase conformer.

FIG. 2 illustrates the embodiment of improving the aptameric adaptiveness in a completely in vitro self-replicating aptameric antigen display according to a key intermediate product due to this process, aptameric antigenic aptameric ribosome-mRNA (AARM) complex. To facilitate the display, the preferred embodiment is to display the antigenic aptamer within a scaffold-fusion protein configuration such that the fusion protein and its cognate messenger RNA can stalled to the ribosomes made possible by introducing a termination codon on to the fused polypeptide such that the hydrolysis of the terminal amino acid of the polypeptide from the tRNA is prevented. Notice that the scaffold fusion gene construct can be designed for either eukaryotic or prokaryotic ribosome display depending on the variance of installing transcription and translation enabling sequences of the 5' primer (Taussig and He, 2003. Ribosome complexes as selection particles for in vitro display and evolution of proteins. U.S. Pat. No. 6,620,587; He and Taussig 1997. N. A. R. 25:5132).

In this embodiment, the charged aptameric antigenic scaffold fusion protein onto the terminal tRNA is stalled on the A-site of ribosome, and fails to release from AARM complex due to the lack of termination codon. Consequently, the entire AARM is selected as an intact physical piece due to the interaction of the cognate protein of the AARM to antibodies/receptors, coated onto the solid phase.

Because of the close association of the mRNA with AAR (aptameric antigen ribosome) in this embodiment, mutations introduced into the message during the RT-PCR reaction are in turn transcribed and translated into the protein phenotype for ready selection. The efficacies of the protein product in the embodiment of AARM can be immediately assessed according to its ability to bind the solid phase conformer.

AARM has a stable association and its components will stay physically attached or glued as one physical piece for as long as two days under 4° C. (Hanes and Pluckthun, 1997. P.N.A.S. 94:4937; He and Taussig 1997. N. A. R. 25:5132; Hanes et al. Nature Biotech. 18:1287). The stalling piece can be fused to the aptamer-antigen protein scaffold, which lends itself a bulky and stable interaction with a ribosome; to render this a stalling interaction, the termination codon of fused Cκ was deleted in the C-terminus, preventing the release of full length fusion protein from the ribosome and cognate mRNA.

Thus, a stable complex of nascent aptameric protein, mRNA and ribosomes, AARM is produced entirely in an in vitro system. Finally the molecular evolved antigen selected by the solid phase, can be amplified by transcription and translation and tested by expressing the pertinent immune reactive B-cell epitopes and detected by traditional western blot analysis according to BEIT assay.

Accordingly, integration of BEIT with ribosome display with built in molecular evolution constitutes a functionally adaptable system in realizing continual improvement of aptamers and antibodies/receptors conformers coated on solid phase. In this preferred embodiment of BEIT, modified aptameric scaffold fusion protein, charged onto the tRNA, associated with its cognate mRNA and overall stalling the ribosomes, will be selected or "fished out" by antibodies/receptors conformer coated on solid phase. Its mRNA will undergo continual rounds of RT-PCR through molecular evolution and the evolved products in turn constrained during each cycle of RT-PCR, AARM with each stage of improved conformity, selected respectively according to the solid phase conformers.

The preferred embodiment is to introduce mutations into the reverse transcribed, amplified copies of DNA by error-prone PCR reactions. The embodiment of solid phase selection of the mutated AARM will ensure the selection of the best fit aptameric antigen due to binding to solid phase conformer antibodies/receptors. Such reiterative rounds can be performed in that the transcription and translation enabled sequences are put back into the core RT-PCR product preferably amplified with an effective primer pair.

Further, the embodiment of a two step RT-PCR reaction will enhance the sensitivity of selection. Henceforth, the first step resides in ensuring effective amplification of selectable mutated subsets, given a condition should this subset of aptameric antigen be present in minute quantities that warrant the use of primer pairs of exhibiting lowest free energy of annealing reaction with the mutated mRNA in AARM complex. Subsequently, re-amplification of this subset of mutated RT-PCR product with less optimal 5' primer for a PCR amplification reaction since it incorporates 5' non-homologous transcription and translation enabling sequence along with the complementary annealing base pair with the initially amplified core PCR product, of which the elevated concentrations of the core RT-PCR product will drive the second RT-PCR reaction. Thus, the final RT-PCR product is suitable for subsequent rounds of aptameric antigen selection in the itinerary process for continual improvement of fine antigenic specificities of high affinity interactions with solid phase conformer antibodies/receptors.

During the RT-PCR reaction, mRNA associated with AARM can be dissociated by EDTA, harvested and purified for RT-PCR reaction. However, the number of copies of mRNA of AARM selected by the solid phase may be scanty in copy numbers, and therefore a majority of the mRNA may be lost during the preparation. In order to increase the sensitivity of RT-PCR reaction based on the few copies of mRNA, the physical manipulation of mRNA will be kept to a minimum. Thus in this embodiment, the mRNA will be directly amplified from the solid phase-bound AARM without neither dissociating it from solid phase nor dissociating it from the AARM complexes. This in situ method thus permits direct use of 3' primer spaced away from the ribosome stalling site thus to avoid steric hindrance of pairing due to bulky ribosomes blocking the nearby sequence close to ribosome stalling sites.

The resulting mRNA is truncated away from the 3' end due to ribosome stalling and thereof interference, which results from shortening distance coverage at the 3' end. Nevertheless, this truncation of the 3' fusion protein (in the specific case of constant light chain $C\kappa$) will not affect the major GFP protein framework, the aptameric sequence region and critical antigenic aptameric specificity.

The preferred embodiment of the invention is to first validate the pre-determined linear sequence in BEIT format, leaving the option of further enhancement by an AARM procedure. Another embodiment is to employ the undetermined random sequences with AARM with the selection from an entire sizable random library of aptameric library. A random oligonucleotide library of four to 16-mer will be prepared with random base assignment constructed and inserted into either one or two sites or three sites of the loops of a scaffold protein with the enabling transcription and translation sequences and adaptable to the complete in vitro ribosome display format. The diversity of the starting DNA library will depend on the nucleotide size of the scaffold that fused to the ribosome stalling protein.

And the single or complex aptameric library will then be transcribed and translated and the large numbers of diverse aptameric antigenic universe that is present in the AARM complexes is vast. Given a 1 kb encoded DNA library members (of the GFP-$C\kappa$ fusion) in a 10 µg of library, the diversity of aptameric library (in the GFP—$C\kappa$ fusion scaffold) will approach $10^{12}$. The embodiment of selecting the correct aptameric antigen representing the transcribed/translated member will follow the identical physical procedures as described for the members of the pre-determined sequences except that the relevant species selected will be in the sub-picogram and femtogram levels.

This aptameric protein scaffold system exhibits a sensitivity of selection at 10 femtograms, which amounts to 1,000 molecule redundancy at the beginning of selection onto solid phase conformers. The redundancy group is considered a related kinship group exhibiting facsimile of geometric shape with detectable binding to conformers. Such a kinship group can therefore be selected by the antibodies or receptor or acceptor. Further selection of a best fit member in the physical form of AARM among the kinship group, will ensure its amplification by RT-PCR. The selected member(s) from the sizable starting aptameric library shall be tested for its utility in eliciting antibodies that block interactions of native antigens and antibodies even though the native antigens do not contain the random aptameric sequences.

The effective neutralization of native antigens by antibodies raised against the selected members of the starting random aptameric protein library attests to a similar conformation of a B-cell epitope exhibited by the native protein vs. that exhibited by the selected aptameric region of aptameric protein. Furthermore, the affinity of the kinship group can be improved via mutation introduced to the DNA that is cognately selected along with the protein it encodes and selectively bound to the solid phase conformers.

The invention embodies selection of biologic relevant antigens without having a prior knowledge of pre-determined sequences will provide additional exploratory space in the absence of structural or sequence information of a physical entity of the antigen. The convalescent sera of an individual recovering from microbial infection, or sera from autoimmune patients or cancer patients will contain immunoreactivities to microbial, bodily or cancerous constituents. Despite the antigenic entities are unknown, the random aptameric library encompassing mimetics for such specificities are likely present due to the sizable aptameric library.

These subsets of aptameric antigenic mimetics can be selected by such immune sera; furthermore, these mimetics selected as such and prepared as recombinant antigens can be employed to elicit antibodies that react or cross-react with the biologically relevant antigens.

The general platform for "adapting" antigenized GFP molecules herein in the ribosome display (RD) format to ensure productive outcome of antigenization by permitting the utmost specificity and sensitivity of the antigen selection method on the base platform, BEIT or further modified on the pre-determined AARM platform; alternatively, antigen selection can be based on the random AARM platform. For the GFP prototype selection, the 7,500 GFP aptameric mRNA (~10 femtograms) is required for antigen-antibody interaction in order for the selection to take place. This will render it a technical feasible and robust technology for selecting antigens at its fittest.

In addition to GFP scaffold, complementarity-determining region (CDR) of immunoglobulin can also serve as the site for accommodating the foreign sequences. Due to thermal instability, the executed, expressible, selectable protein out of the original diverse oligonucleotide library is in reality a subset of that expressed in the thermostable GFP scaffold. Since the immunoglobulin scaffold will suffer insolubility upon insertion, and thereby excluded from the selection. The working of CDR-based pre-determined sequence will be a smaller subset since a significant portion of amino acid combination may only lead to denatured and thereby unselectable proteins; henceforth the geometric space of the diversity of the CDR-based library will be significantly smaller as compared to a random aptameric library in a more thermostable scaffold. However, once a particular amino acid sequence is expressed in immunoglobulin protein scaffold on the ribosome display format, it can then also be subjected to continual improved selection via the AARP selectable platform.

This invention makes improvement on employing CDR region of immunoglobulin for accommodating foreign aptameric peptides at three different levels. The three novel improvements for this particular CDR platform accordingly herein, are (i) since immunoglobulin is thermolabile and thus may not accommodate a large sequence space as compared to GFP, a smaller subset of sequence space in contrast to that accommodated by GFP, may be adaptable into the CDR region. For application of pre-determined peptide sequence, the first major improvement is to place the aptameric sequence by replacement of native sequences instead of inserting a foreign sequence further on top of the native sequence. This will reduce the physical stress of crowding the already tight physical space and reduce the chance of protein denaturation following simultaneously a removal of the native CDR sequence with a replacement of tested antigenic sequence candidate in its stead. Thus by providing pre-determined amino acid sequence in the un-crowded local environment of CDR, this step enhances the viability of assaying the immunogenicity of the candidate sequences.

(ii) The second improvement is to mutate and select the sequence that best fit the ligand on solid phase for selection. The improvement of this limited sequence space from the existing pre-determined sequence via introduced change of the amino acids with the error-prone PCR and evolution is provided uniquely by the selectable in vitro platform. The AARM for the specific selectable immunoglobulin is constructed into a VH-kappa single chain fusion protein, and adaptable on the ribosome display format; (iii) To overcome the restriction of pre-determined amino acid sequence, the third improvement of the immunoglobulin resides in adapting and selecting the right interaction of the encoded aptameric CDR-immunoglobulin from the random sequence aptameric library with the solid phase conformer.

In summary, embodiment of the platform technology by direct amplification of mRNA on AARM with internal primers, followed by reassembly shows two critical advances in antigenic systems-discovery, (i) this technology enables reiterative rounds of selection of aptameric scaffold protein for exquisite specificity and evolved antigenic fit. The conforming, i.e., shaping and re-shaping of the best-fit antigenic specificities can be initiated with pre-determined amino acid sequence, or with a sizable random sequence aptameric proteins. (ii) With the employment of the current aptameric GFP-Cκ RB platform system, the sensitivity is demonstrated at 10 fgm, i.e., 7,500 aptameric GFP-Cκ of approximately 1 kb construct, this platform a minor high affinity antigenic variant even with a presence of as low as 7,500 copies shall captivate the attention of solid phase conformers according to the ribosome display platform (Yang et al., 2007 B. B. R. C. 359: 251). Therefore requirement for both specificity (guaranteed by repetitive selections) and sensitivity (guarantied by sensitive RT-PCR to detect subsets of at the levels of 10 femtogram), are fulfilled in the antigenic discovery system based on random sequence aptameric selection according to the ribosome display platform.

BRIEF DESCRIPTION OF THE DRAWING AND FIGURES

FIG. 1 illustrates the molecular construction of BEIT for antigen selection. In this scheme the half DNA molecules from the 5' end prepared with the transcription and translation enabling sequences, while the 3' half molecules are inserted with the oligonucleotides corresponding to the B-cell epitopes of interest. The reassembled molecules from the two half molecules are ready for BEIT analysis.

FIG. 2 illustrates the ribosome display format for molecular evolution for antigenic fit. The formation of cognate AARM facilitates the next reiterative round of antigenic selection with the prospect of improving the antigenic fit to the solid phase conformer by introducing mutations into the aptameric antigenic peptide region via error-prone RT-PCR, driven by favorable Darwinian selection on solid phase conformers.

FIG. 3 illustrates the enablement of transcription and translation for evaluating the reactivities of translated products in vitro with antibodies raised to the native protein containing the natural pre-determined amino acid sequence. FIG. 3A showed that GFP-IgE chimeric protein were up-scaled by PCR amplification from corresponding pIVEX constructs. The amplified DNA fragments: gfp-6-bc8; gfp-6-de8; gfp-6-fg8; gfp-6-ce2-3L8 and gfp wt, a single 1 kb for the transcription/translation experiments were verified by length. FIG. 3B showed that oligonucleotide and amino acid sequences for presence of novel IgE inserts and used as templates in transcription-translation of corresponding proteins. FIG. 3C showed that In vitro expression of GFP-6-BC8, GFP-6-DE8, GFP-6-FG8, GFP-6-Ch2-3L8, and wild type GFP (GFP WT), evaluated by Western blot analysis by anti GFP antibody binding. FIG. 3D showed that a duplicate blot was probed with anti human IgE antibody.

FIG. 4 illustrates the construction of the scaffold fusion protein for ribosome display platform. Scaffold DNA, i.e., $pGFP_{uv}$ plasmid DNA was used as template with 5' terminal primer containing transcription and translation sequences. Fusion partner cDNA was isolated from murine anti-DNA IgE-producing hybridomas, 26.82 with a PCR primer set. A ligation reaction showed yield of recombinant GFP/Cκ fusion product. The GFP-Cκ fusion product was generated as a template for ribosome display with 5' primer containing the transcription and translation enabling sequences.

FIG. 5 depicts the introduction of random aptameric library on two separate flexible loops of a GFP-Cκ fusion scaffold ribosome display construct. The random library can be selected by the solid phase conformers, and aptameric antigenic mimetics selected from the dual site random sequence libraries as such can be employed for immunization. The insertion/replacement of two pre-determined amino acid sequences as complex antigens can also be implemented in the RD platform for selection for a better fit evolved variant.

FIG. 6 illustrates the construct of VHK ribosome display prototype. The variable heavy chain cDNA was amplified with IGEVH-f and Elbow linker-r (lane 2). The human kappa chain cDNA was amplified with Linker-VL-f and CK-r (lane 3). The scFv or VHKappa cDNA has been generated with overlapping extension PCR by using the forward primer of the heavy chain cDNA and the reverse primer of the kappa chain cDNA (lane 4). Finally the transcription/translation enabled sequences were added as 5' and the entire ribosome display capable VHKappa was prepared with T7-f1/T7-f2 as 5'primers and CK-r as 3' primer with XbaI site of the 3' primer underlined (lane 5 and lane 6).

FIG. 7 illustrates selection of ARMs expressing GFP-Cκ fusion protein on solid phase with dual antibodies: anti-GFP and anti-Cκ by ribosome display. The protocol shows the combination of input PCR-DNA and immobilized anti-GFP and anti-Cκ antibodies used on beads for selection of AARM complexes. The mRNA in selected ARM complexes was extracted with EDTA and RT-PCR performed with the terminal Ym1 and cκ-r pst primer set. The gel shows the recovered cDNA products.

FIG. 8 illustrates selection of ARM by re-assembly PCR via amplified internal primers via in situ RT-PCR. Serial dilutions of the GFP-Cκ fusion PCR construct were used for ribosome display. Recovery of cDNA after selection was by the in situ RT-PCR procedure. After selection of ARM complexes with anti-GFP MAb, RT-PCR recovery reaction was directly performed using Ym-T7 and cκ-r pst in first round PCR (Aa); internal fragment was amplified with rd4-504f and rd-922r in first round PCR (Ab); 5' stuffer region was prepared with Ym-T7 and rd4-574r (Ac); and reassembly PCR was performed with a mix of 5' stuffer region and internal fragments with Ym-T7, rd4-922r/cκ-r in the presence of Cκ template (Ad). The primer sets employed to delineate various PCR products in Panel A were illustrated (B).

GENERAL METHODS AND DEFINITIONS

Protein Scaffold: A protein scaffold is defined as a protein which can provide a region for accommodating a foreign amino acid stretch of sequence as a test for its putative antigenicity. The foreign sequence can be obtained from any regions of any amino acid combination from a protein, although linear sequence from one contiguous region is preferred but a combination of linear sequence from two discrete discontinuous sequences is not excluded. The protein scaffold can be a monomeric polypeptide; alternatively, the protein can form a dimmer, trimer, tetramer and pentamer.

Scaffold Construct: The protein comprises gene with the entire structural entity of the message or spliced message in a contiguous form and the gene are supplemented at the 5' end with the transcription and translation enabling sequence. An aliquot of scaffold is ready for incorporating putative antigenic sequences by assembly PCR reaction.

Scaffold Fusion Construct: The scaffold construct is fused to a ribosome stalling polypeptide with the deletion of the termination codon, and this anti-termination maintains the entire message and protein scaffold fusion protein adherent to the ribosome.

Peptide Aptamer: Aptamer is defined as a peptide sequence with the corresponding oligonucleotide that is inserted into the scaffold construct in any region such as flexible loop, α-helix, β-pleated sheet, β-turn, or hairpin loop, although preferably, the position of the aptamer is more frequently in the flexible loop region bordering the aqueous phase. Furthermore, the mode of presence of aptamer can be an insertion into the native position or by virtue of substituting a portion of the native sequence, consequently deleting the native loop region of the native protein in order to reduce the burden of the incorporated amino acid.

Conformer: A Conformer is a solid phase coated protein, such as monoclonal antibody to conform a single specificity or polyclonal antibodies to conform multiple specificities, or receptor to conform ligands/acceptor, or ligand/acceptors to conform receptor.

Receptor: A protein molecule with recognition specificity for a biologic ligand

Acceptor/ligand: A protein that serve as the endogenous physiological ligand for the receptor during cell-cell communication Peptide Aptameric Oligonucleotide: Oligonucleotides that correspond to the peptide residues from a length of 4 amino acid residues to 16 amino acid residues or from 16 to 25 amino acids. With the placement in the 5' or 3' end of the scaffold construct, the length can be from 4 amino acids to 150 amino acids in length BEIT: This acronym stands for B-cell Epitope Immunization Test. An oligonucleotides specifying a given pre-determined amino acid sequence is placed into scaffold construct with transcription translation enabling sequence; the transcribed and translated product is then tested concerning its the immunoreactivity with monoclonal or polyclonal antibodies raised to the native protein.

In vitro Transcription and Translation: Prokaryotic and eukaryotic reaction mixture or commercial kits are employed for transcription of mRNA and translation of protein from the DNA of scaffold of choice in the BEIT or AARM application.

AARM: This acronym stands for aptameric antigen ribosome message (AARM) complex. Aptameric antigen with pre-determined sequence or random sequence incorporated into the scaffold fusion construct is transcribed and translated in vitro with the mRNA and aptameric antigen attached to ribosomes. Since mRNA of the stalling polypeptide at the 3' end of the aptameric antigen is devoid of the termination codon, the resulting AARM stays as one physical piece of molecular complex AARM-Coupled Molecular Evolution: AARM can be selected via its binding to the solid phase antigen, or acceptor or receptor, and mRNA associated with AAR can then be amplified via reverse transcribed PCR reaction, re-iterative binding of aptameric antigen to the solid phase can be enhanced by introducing mutation into the mRNA via error-prone PCR, and selection for high affinity binding of the aptameric antigen can then be implemented for faster binding of AARM and/or limiting amount of AARM to solid phase conformers.

AARM of Random Library: One or two or three oligonucleotide libraries are constructed within preferably the flexible loop regions of the scaffold fusion constructed, enabled for in vitro transcription and translation.

Description of Particularly Preferred Embodiments
1. Specification of Neutralizing IgE B-Cell Epitope(s)

The preferred embodiment is to enlist all the proteins of Genbank data base and the X-ray information from the Protein Data Bank (PDB), and the proteins is divided into the part of flexible loop region, alpha helix and beta pleated sheet and stalk regions. Predominantly, the loop sequences will be employed as the pre-determined sequences, moreover, to extensively cover the span of the loop regions, the loop will be used as its entirely, i.e., from 4 amino acids to 25 amino acids; alternatively the loop region will be divided into the overlapping amino acid walk from four, five, six, seven, eight, nine up to 16 amino acid walks or length of windows, in order to cover the entire loop regions in a progressive overlapping manner according to the pre-chosen length of amino acid windows. Without knowledge of the X-ray, the computer graphics that predicts the loop regions can be equally accessed and rendered a prediction based on existing commercial softwares such as DNAStar, MacVector.

The sequences can be either directly inserted into the loop region or by substituting and replacing the loop region native sequence with the pre-determined sequences; another preferred embodiment will be to use spacer of small amino acids such as gly-gly for accommodating the sequences of interest; or the sequences are interspaced with cysteine residues with the looping option. The preferred embodiment is to insert the sequences in any position of the loop regions of GFP scaffold published by Protein Data Bank (RCSB PDB). This embodiment also includes the displacement of the entire native loop sequences of GFP with the placement of aptameric antigenic pre-determined sequence or random aptameric peptide library sequences in the GFP scaffold.

Allergic asthma affects approximately 21 million Americans in the US (160 million world-wide). Indeed, allergic asthma is the most common, serious chronic disease of childhood. About nine million children in the heart of the patient population are afflicted with allergic asthma, with the consequence of 12.8 million losses of school days, 200,000 hospital visits per year, negatively impacting their early mental development and life style. In addition to the tangible economic and productivity loss of allergic asthma, the intangible loss of peace of mind: not conforming to a normal social function and dreading anxiety of subsequent attacks. Thus the human sufferings are enormous. Further, interactions of IgE-activated mast cells with smooth muscle cells are now recognized as the main cause of intractable allergic asthma and asthma-related death. And there is an annual death toll of 5,300 tallied among both children and adults. Thus, there is an urgent, unmet medical need to blunt upstream IgE production and inhibit subsequent IgE binding to mast cells.

The preferred embodiment is to place sequence of the IgE B-cell epitopes into the loop regions of GFP in the technology platform. X-ray structure of loops of the CHε2/CHε3 domains engaged in binding to FcεRIα serves the foundation for constructing receptor-binding B-cell epitopes (Garman et al. 2000. Nature. 406: 259). The dimeric CHε3 domain of IgE interacts with a single receptor at two locations: half of CHε2/CHε3 dimer (Site 1) binds along one side of the α2 receptor domain. A conformational change of the other half of CHε2/CHε3 (Site 2) ensues, and permits the binding of the other half molecule to a1 receptor domain (Garman et al. 2000. Nature. 406:259; Robertson. 1993. J. B. C. 268: 12736; Vangelista et al., 1999. J. Clin. Inves. 103: 1571). Thus, the rationale of the active vaccine is to elicit the loop-specific antibodies that block the docking site of Site 1 of the dimeric CHε2/CHε3, prior to its docking on the α2 receptor domain. Further, such antibodies can also neutralize and accelerate IgE clearance by forming IgE and anti-IgE complexes.

Site1-IgE/Domain2-FcεRIα interaction. Twelve amino acids from the IgE, Site 1 and eight amino acids from the α2 receptor domain bury a total of about 860 $Å^2$ of surface area. Surface binding loops of CHε3: including the immunoglobulin-fold of the BC loop (residue 362-365), the DE loop (residue 393-396), the FG loop (residue 424), and CHε2/CHε3: including the CHε2CHε3 linker regions (C2-3 linker) (residue 334-336), are involved in binding to alpha2 receptor domain. Biochemical studies showed that glycosylation of N394 within the DE loop is not required for receptor binding. IgE B-cell epitopes of Site 1 can contain either the core sequences or contain the core sequences along with the flanking sequences from two to six native amino acid residues on each side.

Site 2-IgE/Domain1-FcεRα. Interaction of ten amino acids from the Site 2 with eight amino acids from α1 receptor domain buries approximately 970 $Å^2$. The IgE residues are localized to two distinct segments of CHε2/CHε3: C2-3 linker region (residue 332-337); and the FG loop (residue 424-427). IgE B-cell epitopes of Site 2 can contain either the core sequences or contain the core sequences along with the flanking sequences from two to six native amino acid residues on each side.

The Site1 and Site 2 use overlapping but non-identical sets of IgE residues for receptor binding (Garman et al. 2000. Nature. 406:259; Robertson. 1993. J. B. C. 268: 12736). Thus, despite the fact that non-receptor-bound IgE in solution exhibits two identical symmetrical conformations on CHε2/CHε3 dimer, the stoichiometry of binding of IgE ligand to receptor is 1:1, not 1 to 2 by molecular mass measurement (Keown et al., 1997. E.B.J. 25:471).

There are two symmetrical receptor-docking Site 1 on each free IgE molecule in the solution or in the circulation. Blocking the receptor-docking Site 1 on CHε2/CHε3 half molecule should abrogate IgE sensitization to mast cells. Since the symmetry of the two sites are lost upon docking, antibodies to the Site 1 will not cross-react/or cross-link with the Site 2 (generated only subsequent to receptor docking, and cause a conformational change of cell-bound IgE). Therefore Site 1-specific antibodies will be safe to use since in principle, since it can no longer cross-link IgE sensitized on mast cells. However, it is imperative that antibodies directed at the particular loop of the Site 1 should avoid spurious binding to the neighboring amino acids of Site 1 (involved in receptor docking). These spurious reactivities inherit an unsafe feature since they can cross-link receptor-bound IgE, and cause spontaneous mast cell degranulation without a need for further allergen challenge. It is important that the active vaccine is appropriately designed and tested to evaluate the existence of unsafe antibodies.

2. Specification of Antigenized IgE B-Cell Epitopes in GFP in an In Vitro High-Throughput Protein Platform: Molecular Constructs The first stage of the technology resides in construct a high throughput antigenized GFP as follows. The GFP mutant designated $GFP_{UV}$ was created by DNA shuffling which results in 45-fold greater fluorescence signal relative to wild type GFP, while possessing the same fluorescence characteristic. The chromophore of GFP, consisting of a modified tripeptide, is buried inside the relatively rigid β-can structure is sensitive to signal quenching due to structural perturbation, and therefore is convenient employed as a indication of native folding after inserting aptamers. We select this vector because $GFP_{UV}$ typically has greater expression rates, intracellular yield, and intracellular solubility. The β-can structure formed by 11 β-strands serves to constrain the 11 loops exposed to the aqueous phase. The loop regions represented by the loop 6 (Site 6) was known to resist distortion of conformation were therefore used as cloning sites for oligopeptide B-cell epitopes, i.e., the four loop sequences of Site 1.

Conventional cloning and expression in the prokaryotic and eukaryotic vectors are labor-intensive and time-consuming for completing the assessment of the immunogenicity. As shown in FIG. 1, we devise a strategy to bypass the requirement of these two steps. The immunogenicity of the replaced IgE B-cell epitopes of antigenized GFP can be expediently tested as in vitro transcribed and translated product. Four different receptor-binding epitopes of human IgE were employed to replace the four amino acids of GFP at site or loop 6. This is achieved by virtue of the one-tube reaction of coupling the in vitro transcription/translation procedure by a commercial kit. This strategy consists of the following three steps: (i) PCRI fragment utilizing a pair of primers that amplify the half molecules spanning the T7 transcription start site, Shine-Dalgarno sequence and the beginning of the GFP (delineated by the 5' primer) up to the upstream GFP sequence to loop 6 (delineated by the 3' primer);

(ii) PCR2 fragment utilizing 5' primer consisting of GFP sequences (that pair with the 3' primer of the first PCR fragment) and the eight amino acids that correspond to the loops that bind to the FcϵRIα and 23 oligonucleotides bypassing the native loop 6 sequences; 3' primers including His-tag and T7 terminator delineated by the 3' primer; (iii) assembly of the two half molecules of GFP, the stuffer PCR1 fragment and PCR2, containing the IgE sequences of interest with the His-tag aided in purification.

The execution of the above strategy is as follow: As shown in FIG. 1, a complete expression cassette of wide type GFP was generated using pIVEX control vector GFP (Roche Applied Science) as a template (A). The two primers employed are gfp-f, gatcgagatctcgatcccgcgaaat (forward), and gfp-r, gaacctgcagagcaaaaaacccctcaaga (reverse). This 1 kb PCR product constitutes a 5' T7 promoter, ribosomal binding site (RBS), wide type GFP, followed by 3' linker, His-tag and T7 terminator. This PCR product functioning as a complete in vitro expression cassette is employed as template. In assembly PCR incorporating IgE epitope, PCR1 consisting of 5' regulatory sequence and up to sequence upstream of loop 6, was produced using the above template with forward primer, gfp-f and the reverse primer, gfp#6-r, <u>gtctgccatgatgtatac</u> upstream of loop 6 sequence (FIGS. 1B and D, lane 5). PCR2 containing four different IgE epitopes at loop 6 (FIG. 1B and FIG. 1D, lane 1 to 4) was produced using the same reverse primer, gfp-r, and different forward primers.

The four forward primers are gfp#6-f-bc8, aat <u>gtatacatcatggcagac</u>GTGGTGGACCTGG CACCCAGCAAG ggaatcaaagttaacttcaaaat, gfp#6-f-de8, aat <u>gtatacatcatggcagac</u>AAGCAGCGCAATGGCACGTTAACCggaatcaaagttaacttcaaaat, gfp#6-f-fg8,aat <u>gtatacatcatggcagac</u>CACCCCCACCTGCCCAGGGCCCTC ggaatcaaagttaacttcaaaat, and gfp#6-f-ch2-3L8, aat <u>gtatacatcatggcagac</u>GATTCCAACCCGAGAGGGGTGAGCggaatcaaagttaacttcaaaat. The sequence in the middle (capitalized) encodes different IgE epitopes, and flanking sequences on both sides for the four primers are identical. The 3' flanking sequence is designed for annealing to GFP template for synthesizing PCR2 fragment and 5' flanking sequence, i.e., upstream loop 6 sequence, is for complementing the end of PCR1 fragment for assembly PCR. The reassembled PCR product containing IgE B cell epitopes serves as a functional cassette for transcription and translation (FIGS. 1C and E). The underlined sequence is complementary to the primer, gfp#6-r.

3 Specification of Antigenized IgE B-Cell Epitopes in GFP in an In Vitro High-Throughput Protein-Immunoblot Platform: Protein Expression Immune recognition of the four receptor-binding loops constrained by GFP scaffold by polyclonal anti human IgE antibody was then studied. IgE loop-antigenized GFP were expressed in vitro via a transcription/translation reaction based on *E. coli* lysates (Roche, Rapid Translation System RTS 100 *E. coli* HY kit). In this system, a DNA template and T7 RNA polymerase are coupled with DNA-free *E. coli* lysates, resulting in expression of native GFP with desired replaced antigenic epitopes. The DNA template-based expression cassettes for IgE epitopes of 8 amino acid in length: bc8, de8, fg8 and ch2-3L8 were constructed according to the pIVEX control template with the transcription/translation/termination signals as described above. The quality of the amplified DNA cassettes: gfp-6-bc8; gfp-6-de8; gfp-6-fg8; gfp-6-ce2-3L8 (DNA sequence in small letters) and gfp wt was verified by length of approximately 1.1 kb shown in FIG. 3A, as well as by sequencing shown in FIG. 3B.

The PCR amplified DNA can then be directly employed for transcription/translation-coupled reaction for the protein expression. The newly translated IgE epitope-antigenized GFP were allowed for efficient folding with a cocktail. And integrity of the translated products (in capital letter): GFP-6-BC8, GFP-6-DE8, GFP-6-FG8, GFP-6-C2-3L8 was evaluated by western blot with both anti-GFP and anti-IgE. Efficiency of expression was compared to the wild type GFP. The anti-GFP antibody binding products showed the molecular size, approximately 25.0 kDa, as anticipated for a full-length GFP protein. To preserve the conformation of IgE, the translated products are prepared and steps executed in the native conditions. Efficient expression was observed with all the constructs as determined by the integrity of GFP molecules in each construct. However, anti-IgE did not detect the FG, and DE loops, suggesting that these loops are not presentable in the chimeric molecules. On the other hand, there was a distinctive band observed with GFP-6 containing the Ch2-3L8 protein detected with anti-human IgE antibody (FIG. 3D). The data suggest that the C2-3 linker loop and the BC loop were better constrained in the Site 6 region of GFP. For large scale protein production, the chosen candidates, C2-3 linker loop was cloned into pIVAX and expressed in DH5 cc, and soluble antigenized GFP was purified by the IMAC column.

A detailed assessment of native constrained conformation of IgE B-cell epitopes in the GFP scaffold is as follows: FIG. 3A showed that GFP-IgE chimeric protein were up-scaled by PCR amplification from corresponding pIVEX constructs with pair of primers: 5'-gatcgagatctcgatcccgcgaaat-3' (the common gfp-f; forward primer) and 5'-gaacctgcagagcaaaaaacccctc-3' (the common gfp-r; reverse primer). The amplified DNA fragments: gfp-6-bc8; gfp-6-de8; gfp-6-fg8; gfp-6-ce2-3L8 and gfp wt, a single 1 kb for the transcription/translation experiments were verified by length. FIG. 3B showed that sequences for presence of novel IgE inserts with reverse sequencing primer Rd 4 688r and used as templates in transcription-translation of corresponding proteins.

FIG. 3C showed that In vitro expression of these chimeric GFP-IgE antigenized proteins was performed for 6 hours at 30° C.; after completion, samples were left overnight at 4° C. to allow for efficient folding of newly synthesized protein molecules. The protein was precipitated first by acetone to remove the interfering material in the lysates. Expression of GFP-6-BC8, GFP-6-DE8, GFP-6-FG8, GFP-6-Ch2-3L8, and wild type GFP (GFP WT) was evaluated by Western blot analysis by anti GFP antibody binding (GFP Monoclonal Antibody, purified, mouse clone B34, Covance, Cat. No. MMS-118P, 1:3000, and rat anti mouse kappa, 1:1000). FIG. 3D showed that a duplicate blot was probed with anti human IgE antibody (1:1 mixture of two antibodies: goat anti human IgE-HRP conjugated, Bethyl, Cat. No. A80-108P and goat anti human IgE epsilon-HRP conjugated, Caltag Laboratories, Cat. No. H15707). Translated products resuspended in sample treatment buffer containing 1% NP40 with no SDS, were loaded on gel in native buffer. To diminish background, blots were incubated with goat IgG (2 mg/ml).

4. To Establish a B-Cell Vaccine Systems-Discovery Platform by Showing Minimal Antigenic Epitopes B-cell epitopes are known to accommodate as few as four to five amino acid residues (Mahler et al., 2004. Clin. Exp. Allergy. 34: 115) (4). A preferred embodiment is to find out empirically "the minimal essential amino acids that are required to span in the GFP scaffold. This may ease the thermodynamic constraint to accommodate fewer residues of grafted amino acids necessary by empirical means. According to the X-ray, there are altogether 9 residues (three of C2-3 linker; two of BC loop; three from DE loop and one from FG loop) that are engaged in major interactions with the Y129 and Y131 localized on the pivotal C strand and C'-E region of the receptor D2 regions (In contrast, receptor F strand, FG loop and G strand of D2 contribute in a minor way (Garman et al., 1998. Cell. 95:951)(5). H424 of the FG loop ($H^{424}L^{425}P^{426}R^{427}$) interacts with pivotal anchor residue, Y131. D362 and A364 of the BC loop ($V^{361}D^{362}L^{363}A^{364}P^{365}S^{366}$) interact with the Y131 of the receptor C'-E region. Note-worthily, three important residues of the DE loop ($R^{393}N^{394}G^{395}T^{396}$), RNG 393-395, interact with alanine 126 on receptor, modulating the binding to the critical, pivotal anchor residue, Y129. The preferred embodiment of this invention will be to incorporate the high throughput in vitro transcription/translation for minimal constrainable DE, FG and BC loop amino acid residues for linear antigen capability by replacing the native sequence and also for subsequent improved antigenicity by AARM.

Another embodiment will be to introduce B-cell epitopes with spacers. Thus, the pantameric sequences will be spaced by the flexible spacer, Gly-Gly, since 8-mer in the present length appears tolerated in the GFP scaffold. Third, another embodiment will be to intersperse the pre-determined aptamer within disulfide loop to ensure the antigenicity of peptides that in the linear form may not otherwise reproduce the same antigenicity of that native protein (Christman et al., 1999. Prot. Eng. 12:797; Haak et al., 1997. Int. J. Biol. Mac. 20: 209). With GFP as a thermostable scaffold, cyclization further within the rigid constraining scaffold should serve the purpose of yielding peptide conformations mimicking the native IgE. The embodiment for testing IgE B-cell epitope can be likewise employed for antigen discovery of biologic important residues.

5. To Ensure Success of the Systems-Discovery Platform of IgE B-Cell Epitopes by Adapting Aptameric GFP on Ribosome Display Format To optimize the interaction of pre-determined sequences constrained in the loop, a preferred embodiment is to prepare the IgE B-cell epitopes on GFP fusion scaffold in the AARM format for selection of mutated aptameric sequence that best fit the conformer on solid phase. This embodiment according to rational mutagenesis will consist of the following four steps:

(i) mutating the single position or double positions of the pre-determined amino acid. Thus, the 5' forward oligonucleotide primers (specification) will be synthesized by altering any one base change of the pre-determined amino acid sequence resulting in a different amino acid at each of the five positions, given an aptameric peptide with five pre-determined sequence of amino acids with each position for any possible amino acid residue). This pool of oligonucleotides thus consists of five synthetic reactions. Similarly, another pool of oligonucleotides varying at any two positions of pre-determined sequence of five residues will require 24 oligonucleotide synthesis, i.e., (4×3×2=24 different oligonucleotide insertions). (ii) For each PCR reaction specified, the PCR fragment 2 utilizing one of the primer set will be uniquely synthesized, and each unique subset PCR fragment 2 will be accessible for assembly with PCR1 fragments with the enabling sequences in the PCR reactions. Thus, a mixture consisting of subsets of one variant (19×5=95) or of two variants (19×19×24=8,664 oligo variations) are ready for selection. (iii) The PCR2 fragments are annealed into the GFP-Cκ fusion of the ribosome display format. (iv) The in vitro transcribed and translated ribosome display product with varied aptameric sequence will be selected with polyclonal anti-IgE, or monoclonal anti-IgE and the bound and eluted AARM should contain mRNA that encodes a product with the appropriate, best fit B-cell epitopes. These four integrated processes with the necessary primers and PCR conditions will be executed according to the specifications previously described. This preferred embodiment will rational mutation strategy will generate a significant size of repertoire of molecularly-bred PCR molecules specifically in the aptameric antigenic region such that they offer a considerable size of repertoire to initiate the selection process onto the solid phase without affecting the fusion scaffold.

Enablement of High Affinity and Low Background Selection Via Error Prone PCR and Off-Rate Selection.

To improve the affinity of B-cell epitopes, error-prone PCR will be conducted in the presence of dNTP analogs. The mutation rate can be adjusted with the number of PCR cycles as well as with the concentration of dNTP analogs. With up to 85 μM 8-oxodGTP and 85 μM dNTP, a mutation rate of $6 \times 10^{-2}$/bp can be obtained after 25 cycles of PCR (Zaccolo et al., 1999. J.M.B. 285: 775). The optimal ratios of mutations employing dNTP analogs, required to produce a high affinity aptameric GFP will be obtained empirically. The high affinity of selection can be carried out in the presence of IgE as competitor. Furthermore, the addition of native IgE in an off-rate selection will further enhance the high affinity binding of aptameric GFP to solid phase antibodies. And later ribosome display permits the amplification of mRNA directly from ARM for these winning binders.

Enabling discovery of B-cell epitopes without structural knowledge of the antigen. It is commonplace for the convalescent sera containing the disease-neutralizing antibody without necessarily knowing the antigen it directs against or knowing the structure of the B-cell epitopes. In order to make the antigen systems-discovery platform suitable for this category, platform technology has to be suitable for preparing an aptameric mimetic selected upon the potent neutralizing antibody on the solid phase.

This aspect of exploring the new capacity of such platform will be evaluated for anti-IgE B-cell epitope. It is known that MAb-E25 must react with a protective and neutralizing epitope on IgE molecules. Since the efficacies of passive antibody are already known to be effective in treating human allergic asthma. It will be convenient to determine the conformation what bind to MAb-E25. The antigen system discovery will therefore yield a de novo structure that is a close facsimile of the original antigen structures on IgE molecule, similar to the four IgE B-cell epitopes, alternatively, the binding site of MAb-E25 may accommodate a new epitope or overlapping B-cell epitopes of the existing four epitopes discussed herein.

To achieve this level of selection, a complete random aptameric sequences with no relatedness to any putative receptor-binding site will be employed. The specification for such a library construct was described herein in the previous specification. Thus the selection will consist of the step of (i) employing such a library construct, and prepare the in vitro transcribed/translated aptamers-GFP library in a single test tube. (ii) select the aptameric GFP binders to the solid phase that is coated with MAb-E25. (iii) the eluted mRNA will be amplified by RT-PCR and transform into bacteria. (iv) the recombinant product will be prepared for stimulating anti-IgE response, compared with the specificity of MAb-E25.

The selected aptameric GFP binders will be amplified by RT-PCR and cloned into bacterial expression vector and recombinant produced and purified according to specification, and the product immunogenicity tested in small animals and blocking human IgE binding to mast cells according to specification.

EXAMPLES

Example 1

To Create the GFP-Fusion Platform for Antigen-Discovery Technology

GFP is constructed with replicative and expression capacity for enabling reiterative rounds of phenotype/genotype linked selection, T7 promoter and the Kozak sequence of the eukaryotic system were built into 5' terminal PCR primer (Kozak, 1999. Gene. 234:187). Ribosome display constructs were generated by fusing GFP to the mouse Cκ domain as spacer (He and Taussig, 1997. N. A. R. 25: 5132). The generation of DNA encoding GFP was carried out by PCR amplification using primers Ym1 and gfp-r-not1 on the plasmid PGFP$_{UV}$ as template. DNA fragments encoding Cκ from total RNA extracted from hybridoma cells from rodent anti-DNP IgE-producing hybridoma 16.82 (κ, ε). After RT on the total RNA using random primers, the first-stranded cDNA was amplified by PCR using primers cκ-f not1 and cκ-r pst for Cκ. To generate GFP-Cκ fusions for ribosome display, the PCR fragments encoding GFP were assembled with Cκ, followed by amplification of the products using primers Ym1 and cκ-r pst.

As shown in FIG. 4, overall plan of construct was shown in panel 4A. PGFP$_{UV6}$ plasmid DNA was used as template, with forward primer Ym1, and reverse primer gfp-r-not1. The mouse first strand cDNA was isolated from murine anti-DNA IgE-producing hybridoma, 26.82, and Cκ PCR fragments with forward and reverse primers, cκ-f not1, cκ-r pst, respectively in panel 4B. A ligation reaction showed yield of recombinant GFP/Cκ fusion product in panel 4C. An approximately 1 kb GFP-Cκ fusion product was generated as a template for ribosome display using primer, Ym1 and cκ-r-pst in panel 4D.
2. Random AARM from the Synthetic Library in Single Site Library or Combined Sites Library Previously, we have described the scaffold fusion protein in the ribosome display format. Herein, the design of the aptameric library on at least one loop or more than one loop up to two and three loops of random oligonucleotides corresponding to random aptameric peptide sequences. This permits the conformation of antigenic mimetic to assume the desirable dimension owing to contribution from replacement of one native loop or site with aptameric sequences, or replacement of more than one loop, i.e., two to three native loop or site sequences as a combinatory array of the multiple spatial inputs. One preferred embodiment is to construct each single site reaction, namely the site A, or site B or site C by PCR with appropriate primers. Subsequently, the combined library will be made by assembly PCR reactions with site A and Site B first, followed by site C annealing and PCR amplification. Alternatively, site B and Site C fragments can be annealed, amplified. And the amplified fragments were again followed by a second annealing with Site C and another PCR reassembly of a full length fragment. In another preferred embodiment, two site libraries comprising two fragments of site A and site B can be constructed. This is performed by amplification of fragment A and B respectively with the respective primer pair, followed by the annealing of fragment A and B in a PCR reaction without employing primer pairs.

FIG. 5 showed a one site library construct, Site A, i.e, site 6 from Ala 155 to Ile 161 of one scaffold protein of choice was replaced with a completely randomized 10-mer aptameric library of 30 oligonucleotides. This half molecules comprising the half portion of GFP and the ribosome stalking fragment CK, designated thus as PCR2 fragment. Another fragment designated as PCR1 includes the functional T7 transcription sequence and Kozak sequence for translation. This design permits a stretch of 18 nucleotides overlapping sequences between the PCR1 and PCR2 and thus bridging the PCR1 and PCR2 fragments.

To prevent bias introduced due to a differential pairing/amplification of 5' and 3' primer pair with a particular PCR1+2 fusion product with a putative favorable secondary structure dictated by a subset of library sequences, fusion amplification of two PCR fragment was conducted in the absence of primers. Thus, 1 μg each of PCR1 and PCR2 were paired via the 18 nucleotide homology sequence in the absence of primers for 35 cycles. The hybridization of the overhang of PCR1 and PCR2, is driven entirely by the free energy of the pairing of the internal GFP bridging sequence, and the bases were then filled in via PCR reaction. It is anticipated that each unique oligo on PCR2 may be replicated equally so long as re-annealing of the two half templates was governed by free energy of the 18 bridging sequences. The fused product (PCR1+2, FIG. 5B) was gel purified and approximately one microgram of fused DNA was obtained, which represents a diversity of $7.5 \times 10^{11}$ in this particular library construct.

Furthermore, another one site library, Site B library can be made, the aptamer library at site 8/9 can constructed with same strategy as the site A library (site 6 of GFP in particular) aptameric library as mentioned above. The amplification of PCR1 fragment was performed using forward primers T7xb ext, and the reverse primer, rd4-688r, and that of PCR2 fragment was performed using a library oligo (library 8-9f) and ck-r pst. Similarly, one microgram each of PCR1 and PCR2 fragment were fused by overlap extension for 35 cycles without accompanying primers. The nearly 1.2 kb fused fragment (PCR 1+2 middle panel FIG. 5B) was gel purified and approximately 1 μg purified, representing the diversity of approximately $7.5 \times 10^{11}$ library.

Next we show that the library can be combined. The embodiment of combinatory sites will add to the advantage for furthering diversity ($5.6 \times 10^{22}$); and in enhancing the area of contact with regard to spatial orientation and improved quality of contact. The combinatory library was obtained by using amplified site or loop #6 library as a template for generating PCR1 fragment. Therefore, approximately 1 µg of amplified library site #6 was used in a total of 10 PCR reactions for 5 cycles using primers T7 xb ext and rd4-688r. Amplification of PCR2 was performed likewise for generating library site or loop 8/9. Approximately 1 µg of gel purified PCR 1 and PCR 2 were then used as templates for extension PCR without adding primers (PCR 1+2), right panel in FIG. 5B). A total of 1.4 µg ($1 \times 10^{12}$ molecules) for a 10-mer library of $1.0 \times 10^{10}$, a redundancy of 100 in this original parent library.

3. Choice of VH/VK Family Members and Stability of VHK

VHI family and VKIII family members of immunoglobulin genes are frequently employed for eliciting human antibody responses. Myeloma U266-secreting human IgE (with unknown antigenic specificity) utilizing VH1 and VKIII is employed for constructing single chain Fv antibody as VHK herein. In contrast to single chain Fv antibody (scFv), VHK is energetically a far more stable protein scaffold. The interaction energy of CH contact domain is missing in scFv as compared to natural Fab fragment. VH/VL interface is 710 Å, which represents a relatively weak VH/VL interaction energy typical of Fv fragments; this will render the pairing of VH/VL not efficient for the purpose of immune recognition. Moreover, among the weak interaction of VH/VL is a primary hydrophobic interface for intermolecular interaction, thus resulting in its lower concentration-dependent stability for aggregate formation (Worn and Pluckthun. 2001. J.M.B. 305: 989; Nieba et al., 1997. Prot. Eng. 10: 435). This aggregation complicates the drug development due to its potential to cross-link the target molecule.

Varying linker length form 15 to 25 residues may to some extent inhibits formation of dimer, trimer or tetramer of scFv due to the intervening spacer sequence. In the case of antigenization of pre-determined sequence, multivalent scFv carrying the antigenized IgE B cell epitope will cause spontaneous activation and mast cell degranulation.

It has been demonstrated in scFv, a more thermostable VL domain can stabilize a VH domain of equal or lower stability, and a thermostable VH stabilizes reciprocally a VL domain of equal or less stability (Jung et al. 1999. J. M. B. 294: 163; Worn and Pluckthun. 1998. Biochem. 37: 13120; Proba et al., 1998. J.M.B. 275: 245). Thus, scFv cloned into a plasmid expression vector for a fusion with the kappa constant domain of immunoglobulin including the hinge, was shown highly expressed and stable at high concentration in *E. coli*. (Troth et al., 1999. Phytopatholo. 89: 1015). Thus the invention strategy herein is to fuse VH to VL with appropriate linker, and the VL to the entire human Cκ domain. Thus the stability achieved for the VLCK will in turn stabilize its interaction with VH, which is fused to VL at the 5' end. The construct shown in FIG. 6 was made in the steps as followed.

First, the single-chain Fv (scFv) component was amplified as VH and VL+CL from the U266 cDNA library respectively with the specific primers shown in FIG. 6. Then, during the assembly, the variable heavy chain, VH was fused to VLCL. The following steps were involved: (i) the variable heavy chain cDNA was amplified with IGEVH-f and Elbow linker-r; (ii) the kappa chain was amplified with Linker-VL-f and CK-r. (iii) By using overlapping PCR, these two fragments were joined to generate the VHK cDNA. (iv) To enable the AARM selection process, the T7 promoter was added to the 5' end of scFv PCR product to form the ribosome display format. A VHK cDNA was finally inserted to KS vector with blunt end cloning. This will permit the large preparation of plasmid DNA containing the VHK for PCR-based DNA amplification.

The VH and kappa cDNA were generated with specific primers, and joined with elbow linker, containing 12 amino acid residues (ASTQSPSVFPLT). This 12 amino acid residues linker allowed this recombinant protein to form the stable monomeric VHK. The "elbow" region as a natural extension was well preserved in the junction of CHε1. Using elbow region instead of the gly-gly artificial linker yielded a more stable single chain Fv, i.e., the monomeric VHKappa. Synthetic and rationally mutagenized libraries will be constructed, and in vitro transcribed and translated, and the AARM may be then selected for desirable antigenic specificities. The proof of principle for these complete procedures was described in library-containing GFP scaffold.

Construct of VHK ribosome display prototype was executed in five steps. (i) The variable heavy chain cDNA was amplified with IGEVH-f (31 mer, 5-caccatggac tggacctgga tcctcttctt g-3) and Elbow linker-r (48 mer, 5-tgtcagagga aagacggaag gggattgtgt tgaggctgag gagacggt-3), has shown in lane (ii) The kappa chain cDNA was amplified with Linker-VL-f (38 mer, 5-gtctttcctc tgacaga(c/a)at (t/g)$_g$(t/c)gatgac(c/g) cagtctcc-3) and CK-r (29 mer, 5-gctctagaac actctcccct gttgaagct-3), has shown in lane 3. (iii) The scFv cDNA has been generated with overlapping extension PCR by using the forward primer of the heavy chain cDNA and the reverse primer of the kappa chain cDNA, the product has shown in the lane 4. (iv) The T7 promoter DNA sequence was added the 5' end of the VH-kappa cDNA with T7-f2 (44 mer, 5-TAATAC-GACT CACTATAgag ggagccacca tggactggac ctgg-30, and CK-r (29 mer, 5-gc<u>tctaga</u>ac actctcccct gttgaagct-3). XbaI site was labeled with underline. (v) The final step was to add additional 20 nucleotides on the 5' end of the T7 promoter, with T7-f1 (41 mer, 5-<u>agatct</u>cgat cccgcgaaat taatacgact cactatagag g-3). The PCR products were separated from agarose gel, and purified with QIAGEN gel extraction kit. Panel A showed junction DNA sequences of T7 promoter, elbow linker, and 3' end of the kappa sequence DNA with under line. Panel B. 10 µl PCR products of VHK cDNA were separated with 0.8% agarose TAE gel. 1 kb markers (ln 1); PCR of the variable heavy chain (ln 2); PCR of the kappa chain (ln 3); PCR of VHK (ln 4); PCR T7-VH-kappa chain (ln 5): and PCR of ext-T7-Vh-kappa chain (ln 6).

4. Demonstration of Antigen Selection with Two Different Antibodies on Solid Phase Reaction In Vitro This proof of feasibility of selection of the above GFP-CK fusion RD construct by anti-GFP as well as anti-Cκ on solid phase were demonstrated: Method (i): Standard post-selection recovery of mRNA for prototypic antigenized GFP selection with terminal primers:

To evaluate the ribosome display selection and different cDNA recovery procedures after RT-PCR, we therefore chose primer-efficient construct such as Ym1 with the design of T7 ext followed by Kozak along with 16 homologous GFP nucleotides. The selection of complexes was based on binding of epitopes expressed on the Cκ3') region, or on the GFP (5') moiety by immobilized anti-Cκ and anti-GFP antibodies respectively. Different input amounts of DNA were subjected to ribosome display and selection on anti-Cκ and anti-GFP coupled beads. Recovery of cDNA post-selection was by elution and purification of mRNA from ribosome complexes followed by RT-PCR (Hanes and Pluckthun, 1997. P.N.A.S. 94: 4937).

Method (i) was executed as follows: PCR construct DNA was added to 50 µl rabbit reticulocyte lysate at 30° C. for 60 min. Hydrophobic tosyl-activated Dynabeads (2.8 mm with p-toluene sulfonyl, 1.3 g/ml) were coupled with anti-GFP antibody or anti-Cκ antibody, overnight at 4° C. For selection on beads coupled with anti-GFP antibody or anti-Cκ antibody, the translation mixture was diluted on ice at 1:8 ratio with 1× phosphate-buffered saline (PBS) containing 5 mM Mg acetate before adding to 16-24 μl beads and incubated at 4° C. for 2 h. After washes, DNA was recovered by one of the two methods: (i) mRNA was eluted from the ribosome complexes with 10 μl PBS/20 mM EDTA, followed by purification prior to RT-PCR, or (ii) RT-PCR was performed directly on the ribosome complexes (in situ recovery) with a 3' primer annealing upstream of the stalled ribosome (19). To eliminate possible input DNA contamination, 10 U RNase-free DNase I (NEB) was added to eluted mRNA or complexes and incubated for 20 min at 37° C. OmniScript RT kit was used to perform cDNA synthesis with appropriate primers, i.e., internal primers for method (i), and ck-r pst for method (ii). Follow-up full length assembly PCR was performed with 5' primers, Ym1 or Ym-T7 and 3' primer cκ-r pst for 35 cycles of 94° C. for 30 seconds, 60° C. for 1 min and 72° C. for 1 min.

As shown in FIG. 7, a 1 kb band of recovered cDNA was seen after selection by either anti-Cκ or anti-GFP with only as high as initial 100 ng input construct DNA (lanes 1 and 4). In contrast, no cDNA was detected in the control beads without coupled antibody with 100 ng input construct (lane 7). Reducing the input of GFP-Cκ DNA construct by 100 fold abatement successively to 1 ng and to 10 pg, resulted in no recovery of a visible band after one cycle (lanes 2, 3 for anti-Cκ and 5, 6 for anti-GFP). Thus, this method of eluting free mRNA for RT-PCRT reaction requires a higher concentration of start-up DNA at 100 ng per reaction. Therefore, this specification shows the feasibility for antigen discovery with either antigenic B-cell epitope, that of GFP or that of kappa chain. However, this "one sweep" of complete construct with terminal primer can miss the minor evolved variant at 100 ng sensitivity of input antigens. Therefore the improved specification for sensitivities to render analysis of minor variants is presented as follows:

Method (ii) Sensitive post-selection recovery of mRNA for prototypic antigenized GFP. To increase the sensitivity of selection, we chose (i) to recover DNA directly from ribosome complexes with in situ RT-PCR without eluting the mRNA from ARM; (ii) to streamline PCR reaction with more efficient internal primers encompassing a loop region of interest, followed by reassembly PCR with stuffer cassette.

In this experiment, input DNA was employed over a six log concentration range (10 ng, 10 pg and 10 fgm), corresponding to $10^{10}$, $10^7$ and $10^4$ molecules, respectively. After ribosome display and selection on the beads coupled by anti-GFP, the in situ RT-PCR procedure was performed directly on the selected ribosome complexes using an optimal primer pair as follows. Ym-T7 was prepared with a further 10 nucleotide truncation of the non-homologous sequence 5' to the T7 sequence along with an internal 3' G/C ratio streamlined primer, rd4-922-r, away from the ribosome binding site. This step increases the efficiency of mRNA recovery for RT-PCR bypassing the requirement of isolating mRNA from ARM complexes.

As shown in FIG. 8, the 1 kb band was recovered via the RT-PCR reaction (Lane 1 panel a), and there was also a vague band in lane 2, and the material on band 3 was not noticeable according to ethidium bromide staining followed by UV detection. Thus the in situ PCR with re-designed primer set has improved the sensitivity of detection from 100 ng starting material (note: previous lane 4, FIG. 8) to approximately 10 pg (lane 2, FIG. 8Aa). Since sensitivity is a critical issue in detecting rare copies of mRNA carrying a unique specificity in a library construct, the above flanking primers such as Ym-T7 may be still capable of being streamlined since Ym-T7 still contains in part non-homologous sequence that does not pair with mRNA of AARM of GFP-CK construct. This may explain the barely visible band in lane 2 and lack of detection in lane 3 of FIG. 8Aa during the first round RT-PCR product.

Therefore we reason that although the first round RT-PCR product escapes detection via UV instrumentation (normally $10^8$ molecules are required for visibility by UV), there could be already present abundant copies of RT-PCR products identifiable upon another round of PCR reaction. To enhance the recovery of DNA, a partial RT-PCR fragment after ribosome display, internal primers, rd4-504f and rd4-922r were synthesized as a fragment encompassing the critical region of loop 6 and 8/9 of GFP intended for an inserted peptide library. 5' stuffer fragment was prepared with Ym1 or Ym-T7 with rd4-574r. The RT-PCR products were then assembled into the full-length ribosome display enabled cassette by PCR overlapping the added Cκ domain with terminal primers. FIG. 8Ab showed that PCR bands of 419 bp were indeed detected in all three lanes of equal intensity from first round in situ PCR products with rd4-504f and rd4-922r internal primer set. Therefore, we demonstrated the feasibility of recovering limiting amount of starting material from as few as 10 fgm GFP-Cκ construct by using optimized, completely homologous highly efficient 5' and 3' internal primers. Thus with the second technique of preparing internal fragments in a two-step process, high sensitivity of the recovery is achieved at 10 fgm of starting material.

Next, to fully reassembly an RD-enabled product for re-iterative selection, a stuffer region encompassing the C-terminal part of the half molecules of GFP-Cκ was prepared with the primer set, YM-T7 and rd 457r (FIG. 8Ac). Ribosome display enabled entities were reassembled with 3' internal fragment prepared (FIG. 8Ab) and the 5' GFP stuffer region (FIG. 8Ac) with assembly primer set Ym-T7 and rd4-922r. Therefore sensitivity up to 10 fgm of starting material was achieved even in the first round of solid phase selection and assembly by combining the techniques in situ PCR in conjunction with amplifying the internal fragments, followed by full assembly with stuffer cassette containing the ribosome enabling transcription/translation sequences (FIG. 8Ad).

In summary, execution of the platform technology by direct amplification of mRNA on ARM with internal primers, followed by reassembly shows two important merits, (i) this technology enables re-iterative rounds of selection of aptameric GFP for exquisite specificity and evolved antigenic fit. (ii) With the utmost sensitivity demonstrated at 10 fgm, i.e., 7,500 aptameric GFP, this platform will captivate the attention of minor high affinity antigenic variant even with a presence of as low as 7,500 copies (Yang et al. 2007. B.B.R.C. 359:257). Therefore both specificity (guaranteed by repetitive selection) and sensitivity (10 femtogram subset) are fulfilled in the antigenic systems-discovery platform.

I claim:

1. An aptameric IgE peptide fused in a protein scaffold wherein the IgE peptide is chosen from the group consisting of SEQ ID NO: 6, SEQ ID NO: 8, SEQ ID NO: 10, SEQ ID NO: 14, SEQ ID NO: 16, and SEQ ID NO: 18, and wherein the aptameric IgE peptidic protein scaffold is a fusion protein.

2. A pharmaceutical composition comprising one or more aptameric IgE peptides of claim 1 fused to a protein scaffold as fusion proteins.

3. A synthetic oligonucleotide encoding an aptameric IgE peptide of claim 1 wherein the oligonucleotide encoding the aptameric IgE peptide is recombinantly fused to a polynucleotide encoding a protein scaffold as a fusion polynucleotide.

4. A synthetic oligonucleotide encoding an aptameric IgE peptide of claim 1 wherein the oligonucleotide is chosen from the group consisting of SEQ ID NO: 5, SEQ ID NO: 7, SEQ ID NO: 9, SEQ ID NO: 13, SEQ ID NO: 15, and SEQ ID NO: 17, and wherein said synthetic oligonucleotide encoding the aptameric IgE peptide is fused to a polynucleotide encoding a protein scaffold as a fusion polynucleotide.

5. A pharmaceutical composition comprising one or more fusion polynucleotides of claim 3 or 4.

6. A pharmaceutical composition comprising one or more fusion proteins encoded by one or more fusion polynucleotides of claim 5.

7. A method of administering one or more aptameric IgE peptides fused to a protein scaffold of claim 2 as fusion proteins to patients to ameliorate IgE-mediated allergic diseases consisting of allergic asthma, allergic rhinitis, atopic dermatitis, allergic conjunctivitis, allergic urticaria, allergic angiodema, and IgE-mediated anaphylactic shock.

8. A method of administering one or more aptameric IgE peptides fused to a protein scaffold of claim 6 as fusion proteins to allergic patients for ameliorating IgE-mediated allergic diseases.

9. A method of administering one or more fusion polynucleotides of claim 5 to allergic patients for ameliorating IgE-mediated allergic diseases.

10. A method of generating aptameric IgE oligonucleotides fused to a polynucleotide encoding a protein scaffold as fusion polynucleotides, which are transcribed as mRNA, translated and selected by binding to high affinity IgE Fc receptors or neutralizing anti-IgE antibodies on the solid phase via protein display, wherein the selected mRNA is reverse transcribed by error-prone RT-PCR, and wherein the aptameric IgE oligonucleotide to initiate selection via protein display is chosen from the group consisting of SEQ ID NO: 5, SEQ ID NO: 7, SEQ ID NO: 9, SEQ ID NO: 13, SEQ ID NO: 15, and SEQ ID NO: 17, and wherein the selected binder aptameric IgE oligonucleotides fused to the polynucleotide selected by protein display are re-iteratively selected, and selected aptameric IgE oligonucleotides are sequenced, whereby the selected binder aptameric IgE fusion polynucleotide, and its recombinantly produced fusion protein are employed as vaccine for ameliorating IgE-mediated allergic diseases.

11. A method of administering one or more fusion proteins of claim 10 to allergic patients for ameliorating IgE-mediated allergic diseases.

12. A method of administering one or more fusion polynucleotides of claim 10 to allergic patients for ameliorating IgE-mediated allergic diseases.

13. The fusion protein of claim 1, wherein the protein scaffold is green fluorescent protein or a single chain Fv antibody.

14. The method of claim 10, wherein aptameric IgE oligonucleotides fused to a polynucleotide encoding a protein scaffold as fusion polynucleotides is selected by binding to high affinity IgE Fc receptors or neutralizing anti-IgE antibodies on the solid phase by protein display consisting of phages and yeasts.

* * * * *

SEQUENCE LISTING

<160> NUMBER OF SEQ ID NOS: 28

<210> SEQ ID NO 1
<211> LENGTH: 720
<212> TYPE: DNA

<213> ORGANISM: Aequorea victoria

<400> SEQUENCE: 1

```
atgagtaaag gagaagaact tttcactgga gttgtcccaa ttcttgttga attagatggt    60
gatgttaatg ggcacaaatt ttctgtcagt ggagagggtg aaggtgatgc aacatacgga   120
aaacttaccc ttaaatttat ttgcactact ggaaaactac ctgttccatg gccaacactt   180
gtcactactt tctcttatgg tgttcaatgc ttttcccgtt atccggatca tatgaaacgg   240
catgactttt tcaagagtgc catgcccgaa ggttatgtac aggaacgcac tatatctttc   300
aaagatgacg gaactacaa gacgcgtgct gaagtcaagt ttgaaggtga tacccttgtt   360
aatcgtatcg agttaaaagg tattgatttt aaagaagatg aaacattct cggacacaaa   420
ctcgagtaca actataactc acacaatgta tacatcacgg cagacaaaca aaagaatgga   480
atcaaagcta acttcaaaat tcgccacaac attgaagatg gatccgttca actagcagac   540
cattatcaac aaaatactcc aattggcgat ggccctgtcc ttttaccaga caaccattac   600
ctgtcgacac aatctgccct ttcgaaagat cccaacgaaa agcgtgacca catggtcctt   660
cttgagtttg taactgctgc tgggattaca catggcatgg atgagctcta caataatga   720
```

<210> SEQ ID NO 2
<211> LENGTH: 239
<212> TYPE: PRT
<213> ORGANISM: Aequorea victoria

<400> SEQUENCE: 2

```
Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Ser Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys
```

<210> SEQ ID NO 3
<211> LENGTH: 1920
<212> TYPE: DNA
<213> ORGANISM: Homo sapiens

<400> SEQUENCE: 3

| | | | | | |
|---|---|---|---|---|---|
| ggatccctgc | cacggggtcc | ccagctcccc | catccaggcc | cccaggctg | atgggcgctg | 60 |
| gcctgaggct | ggcactgact | aggttctgtc | ctcacagcct | ccacacagag | cccatccgtc | 120 |
| ttccccttga | cccgctgctg | caaaaacatt | ccctccaatg | ccacctccgt | gactctgggc | 180 |
| tgcctggcca | cgggctactt | cccggagccg | gtgatggtga | cctgggacac | aggctccctc | 240 |
| aacgggacaa | ctatgacctt | accagccacc | accctcacgc | tctctggtca | ctatgccacc | 300 |
| atcagcttgc | tgaccgtctc | gggtgcgtgg | gccaagcaga | tgttcacctg | ccgtgtggca | 360 |
| cacactccat | cgtccacaga | ctgggtcgac | aacaaaacct | tcagcggtaa | gagagggcca | 420 |
| agctcagaga | ccacagttcc | caggagtgcc | aggctgaggg | ctggcagagt | gggcaggggt | 480 |
| tgaggggtg | ggtgggctca | aacgtgggaa | cacccagcat | gcctgggac | ccgggccagg | 540 |
| acgtgggggc | aagaggaggg | cacacagagc | tcagagaggc | caacaaccct | catgaccacc | 600 |
| agctctcccc | cagtctgctc | cagggacttc | accccgccca | ccgtgaagat | cttacagtcg | 660 |
| tcctgcgacg | gcgcgggca | cttccccccg | accatccagc | tcctgtgcct | cgtctctggg | 720 |
| tacaccccag | ggactatcaa | catcacctgg | ctggaggacg | ggcaggtcat | ggacgtggac | 780 |
| ttgtccaccg | cctctaccac | gcaggagggt | gagctggcct | ccacacaaag | cgagctcacc | 840 |
| ctcagccaga | agcactggct | gtcagaccgc | acctacacct | gccaggtcac | ctatcaaggt | 900 |
| cacacctttg | aggacagcac | caagaagtgt | gcaggtacgt | tcccacctgc | cctggtggcc | 960 |
| gccacggagg | ccagagaaga | ggggcgggtg | ggcctcacac | agccctccgg | tgtaccacag | 1020 |
| attccaaccc | gagaggggtg | agcgcctacc | taagccggcc | cagcccgttc | gacctgttca | 1080 |
| tccgcaagtc | gcccacgatc | acctgtctgg | tggtggacct | ggcacccagc | aaggggaccg | 1140 |
| tgaacctgac | ctggtcccgg | gccagtggga | agctgtgaa | ccactccacc | agaaaggagg | 1200 |
| agaagcagcg | caatggcacg | ttaaccgtca | cgtccaccct | gccggtgggc | acccgagact | 1260 |
| ggatcgaggg | ggagacctac | cagtgcaggg | tgacccaccc | ccacctgccc | agggccctca | 1320 |
| tgcggtccac | gaccaagacc | agcggtgagc | catgggcagg | ccggggtcgt | ggggggaaggg | 1380 |
| agggagcgag | tgagcgggc | ccgggctgac | cccacgtctg | gccacaggcc | cgcgtgctgc | 1440 |
| cccggaagtc | tatgcgtttg | cgacgccgga | gtggccgggg | agccgggaca | agcgcaccct | 1500 |
| cgcctgcctg | atccagaact | tcatgcctga | ggacatctcg | gtgcagtggc | tgcacaacga | 1560 |
| ggtgcagctc | ccggacgccc | ggcacagcac | gacgcagccc | cgcaagacca | agggctccgg | 1620 |
| cttcttcgtc | ttcagccgcc | tggaggtgac | cagggccgaa | tgggagcaga | agatgagtt | 1680 |
| catctgccgt | gcagtccatg | aggcagcgag | ccctcacag | accgtccagc | gagcggtgtc | 1740 |
| tgtaaatccc | ggtaaatgac | gtactcctgc | ctccctccct | cccagggctc | catccagctg | 1800 |
| tgcagtgggg | aggactggcc | agaccttctg | tccactgttg | caatgacccc | aggaagctac | 1860 |
| ccccaataaa | ctgtgcctgc | tcagagcccc | agtacaccca | ttcttgggag | cgggcagggc | 1920 |

<210> SEQ ID NO 4
<211> LENGTH: 574
<212> TYPE: PRT
<213> ORGANISM: Homo sapiens

<400> SEQUENCE: 4

```
Met Asp Trp Thr Trp Ile Leu Phe Leu Val Ala Ala Thr Arg Val
 1               5                  10                  15

His Ser Gln Thr Gln Leu Val Gln Ser Gly Ala Glu Val Arg Lys Pro
                20                  25                  30

Gly Ala Ser Val Arg Val Ser Cys Lys Ala Ser Gly Tyr Thr Phe Ile
            35                  40                  45

Asp Ser Tyr Ile His Trp Ile Arg Gln Ala Pro Gly His Gly Leu Glu
        50                  55                  60

Trp Val Gly Trp Ile Asn Pro Asn Ser Gly Gly Thr Asn Tyr Ala Pro
 65                  70                  75                  80

Arg Phe Gln Gly Arg Val Thr Met Thr Arg Asp Ala Ser Phe Ser Thr
                85                  90                  95

Ala Tyr Met Asp Leu Arg Ser Leu Arg Ser Asp Asp Ser Ala Val Phe
               100                 105                 110

Tyr Cys Ala Lys Ser Asp Pro Phe Trp Ser Asp Tyr Tyr Asn Phe Asp
            115                 120                 125

Tyr Ser Tyr Thr Leu Asp Val Trp Gly Gln Gly Thr Thr Val Thr Val
        130                 135                 140

Ser Ser Ala Ser Thr Gln Ser Pro Ser Val Phe Pro Leu Thr Arg Cys
145                 150                 155                 160

Cys Lys Asn Ile Pro Ser Asn Ala Thr Ser Val Thr Leu Gly Cys Leu
                165                 170                 175

Ala Thr Gly Tyr Phe Pro Glu Pro Val Met Val Thr Trp Asp Thr Gly
            180                 185                 190

Ser Leu Asn Gly Thr Thr Met Thr Leu Pro Ala Thr Thr Leu Thr Leu
        195                 200                 205

Ser Gly His Tyr Ala Thr Ile Ser Leu Leu Thr Val Ser Gly Ala Trp
        210                 215                 220

Ala Lys Gln Met Phe Thr Cys Arg Val Ala His Thr Pro Ser Ser Thr
225                 230                 235                 240

Asp Trp Val Asp Asn Lys Thr Phe Ser Val Cys Ser Arg Asp Phe Thr
                245                 250                 255

Pro Pro Thr Val Lys Ile Leu Gln Ser Ser Cys Asp Gly Gly Gly His
            260                 265                 270

Phe Pro Pro Thr Ile Gln Leu Leu Cys Leu Val Ser Gly Tyr Thr Pro
        275                 280                 285

Gly Thr Ile Asn Ile Thr Trp Leu Glu Asp Gly Gln Val Met Asp Val
        290                 295                 300

Asp Leu Ser Thr Ala Ser Thr Thr Gln Glu Gly Glu Leu Ala Ser Thr
305                 310                 315                 320

Gln Ser Glu Leu Thr Leu Ser Gln Lys His Trp Leu Ser Asp Arg Thr
                325                 330                 335

Tyr Thr Cys Gln Val Thr Tyr Gln Gly His Thr Phe Glu Asp Ser Thr
            340                 345                 350

Lys Lys Cys Ala Asp Ser Asn Pro Arg Gly Val Ser Ala Tyr Leu Ser
        355                 360                 365

Arg Pro Ser Pro Phe Asp Leu Phe Ile Arg Lys Ser Pro Thr Ile Thr
        370                 375                 380

Cys Leu Val Val Asp Leu Ala Pro Ser Lys Gly Thr Val Asn Leu Thr
385                 390                 395                 400

Trp Ser Arg Ala Ser Gly Lys Pro Val Asn His Ser Thr Arg Lys Glu
```

```
                    405                 410                 415
Glu Lys Gln Arg Asn Gly Thr Leu Thr Val Thr Ser Thr Leu Pro Val
            420                 425                 430

Gly Thr Arg Asp Trp Ile Glu Gly Thr Tyr Gln Cys Arg Val Thr
            435                 440                 445

His Pro His Leu Pro Arg Ala Leu Met Arg Ser Thr Thr Lys Thr Ser
        450                 455                 460

Gly Pro Arg Ala Ala Pro Glu Val Tyr Ala Phe Ala Thr Pro Glu Trp
465                 470                 475                 480

Pro Gly Ser Arg Asp Lys Arg Thr Leu Ala Cys Leu Ile Gln Asn Phe
                485                 490                 495

Met Pro Glu Asp Ile Ser Val Gln Trp Leu His Asn Glu Val Gln Leu
            500                 505                 510

Pro Asp Ala Arg His Ser Thr Thr Gln Pro Arg Lys Thr Lys Gly Ser
            515                 520                 525

Gly Phe Phe Val Phe Ser Arg Leu Glu Val Thr Arg Ala Glu Trp Glu
        530                 535                 540

Gln Lys Asp Glu Phe Ile Cys Arg Ala Val His Glu Ala Ala Ser Pro
545                 550                 555                 560

Ser Gln Thr Val Gln Arg Ala Val Ser Val Asn Pro Gly Lys
                565                 570

<210> SEQ ID NO 5
<211> LENGTH: 24
<212> TYPE: DNA
<213> ORGANISM: Homo sapiens

<400> SEQUENCE: 5
gtggtggacc tggcacccag caag                                          24

<210> SEQ ID NO 6
<211> LENGTH: 8
<212> TYPE: PRT
<213> ORGANISM: Homo sapiens

<400> SEQUENCE: 6

Val Val Asp Leu Ala Pro Ser Lys
1               5

<210> SEQ ID NO 7
<211> LENGTH: 24
<212> TYPE: DNA
<213> ORGANISM: Homo sapiens

<400> SEQUENCE: 7
aagcagcgca atggcacgtt aacc                                          24

<210> SEQ ID NO 8
<211> LENGTH: 8
<212> TYPE: PRT
<213> ORGANISM: Homo sapiens

<400> SEQUENCE: 8

Lys Gln Arg Asn Gly Thr Leu Thr
1               5

<210> SEQ ID NO 9
<211> LENGTH: 24
<212> TYPE: DNA
<213> ORGANISM: Homo sapiens
```

```
<400> SEQUENCE: 9 caccccacc tgcccagggc cctc                                              24

<210> SEQ ID NO 10
<211> LENGTH: 8
<212> TYPE: PRT
<213> ORGANISM: Homo sapiens

<400> SEQUENCE: 10

His Pro His Leu Pro Arg Ala Leu
1               5

<210> SEQ ID NO 11
<211> LENGTH: 24
<212> TYPE: DNA
<213> ORGANISM: Homo sapiens

<400> SEQUENCE: 11
gattccaacc cgagaggggt gagc                                             24

<210> SEQ ID NO 12
<211> LENGTH: 8
<212> TYPE: PRT
<213> ORGANISM: Homo sapiens

<400> SEQUENCE: 12

Asp Ser Asn Pro Arg Gly Val Ser
1               5

<210> SEQ ID NO 13
<211> LENGTH: 18
<212> TYPE: DNA
<213> ORGANISM: Homo sapiens

<400> SEQUENCE: 13
gtggacctgg cacccagc                                                    18

<210> SEQ ID NO 14
<211> LENGTH: 6
<212> TYPE: PRT
<213> ORGANISM: Homo sapiens

<400> SEQUENCE: 14

Val Asp Leu Ala Pro Ser
1               5

<210> SEQ ID NO 15
<211> LENGTH: 12
<212> TYPE: DNA
<213> ORGANISM: Homo sapiens

<400> SEQUENCE: 15
cgcaatggca cg                                                          12

<210> SEQ ID NO 16
<211> LENGTH: 4
<212> TYPE: PRT
<213> ORGANISM: Homo sapiens

<400> SEQUENCE: 16

Arg Asn Gly Thr
1
```

```
<210> SEQ ID NO 17
<211> LENGTH: 12
<212> TYPE: DNA
<213> ORGANISM: Homo sapiens

<400> SEQUENCE: 17
cacctgccca gg                                                           12

<210> SEQ ID NO 18
<211> LENGTH: 4
<212> TYPE: PRT
<213> ORGANISM: Homo sapiens

<400> SEQUENCE: 18

His Leu Pro Arg
1

<210> SEQ ID NO 19
<211> LENGTH: 18
<212> TYPE: DNA
<213> ORGANISM: Homo sapiens

<400> SEQUENCE: 19
acccgagagg ggtgagcg                                                     18

<210> SEQ ID NO 20
<211> LENGTH: 6
<212> TYPE: PRT
<213> ORGANISM: Homo sapiens

<400> SEQUENCE: 20

Asn Pro Arg Gly Val Ser
1               5

<210> SEQ ID NO 21
<211> LENGTH: 25
<212> TYPE: DNA
<213> ORGANISM: Aequorea victoria

<400> SEQUENCE: 21
gatcgagatc tcgatcccgc gaaat                                             25

<210> SEQ ID NO 22
<211> LENGTH: 25
<212> TYPE: DNA
<213> ORGANISM: Aequorea victoria

<400> SEQUENCE: 22
gaacctgcag agcaaaaaac ccctc                                             25

<210> SEQ ID NO 23
<211> LENGTH: 31
<212> TYPE: DNA
<213> ORGANISM: Homo sapiens

<400> SEQUENCE: 23
caccatggac tggacctgga tcctcttctt g                                      31

<210> SEQ ID NO 24
<211> LENGTH: 48
<212> TYPE: DNA
<213> ORGANISM: Homo sapiens

<400> SEQUENCE: 24
```

```
tgtcagagga aagacggaag gggattgtgt tgaggctgag gagacggt        48

<210> SEQ ID NO 25
<211> LENGTH: 38
<212> TYPE: DNA
<213> ORGANISM: Homo sapiens

<400> SEQUENCE: 25
gtctttcctc tgacagacat tgtgatgacc cagtctcc                  38

<210> SEQ ID NO 26
<211> LENGTH: 29
<212> TYPE: DNA
<213> ORGANISM: Homo sapiens

<400> SEQUENCE: 26
gctctagaac actctcccct gttgaagct                            29

<210> SEQ ID NO 27
<211> LENGTH: 44
<212> TYPE: DNA
<213> ORGANISM: T7 phage

<400> SEQUENCE: 27
taatacgact cactatagag ggagccacca tggactggac ctgg           44

<210> SEQ ID NO 28
<211> LENGTH: 41
<212> TYPE: DNA
<213> ORGANISM: T7 phage

<400> SEQUENCE: 28
agatctcgat cccgcgaaat taatacgact cactatagag g              41
```